US012633389B1

(12) United States Patent
Smith et al.

(10) Patent No.: US 12,633,389 B1
(45) Date of Patent: May 19, 2026

(54) SYSTEMS AND METHODS FOR GENERATING USER INTERFACE DATA ASSOCIATED WITH ADHERENCE INTERVENTION DATA

(71) Applicant: RxAnte, Inc., Portland, ME (US)

(72) Inventors: Daniel Smith, Bedford, MA (US); Shawn Hallinan, Shrewsbury, MA (US); Jonathan Korn, Somerville, MA (US); Josh Peterson, Grand Rapids, MI (US); Loren Lidsky, Boston, MA (US); Joshua Benner, McLean, VA (US)

(73) Assignee: RXANTE, LLC, Portland, ME (US)

( * ) Notice: Subject to any disclaimer, the term of this patent is extended or adjusted under 35 U.S.C. 154(b) by 277 days.

(21) Appl. No.: 17/575,111

(22) Filed: Jan. 13, 2022

Related U.S. Application Data

(60) Provisional application No. 63/138,115, filed on Jan. 15, 2021.

(51) Int. Cl.
G16H 20/10 (2018.01)
G16H 10/60 (2018.01)
(52) U.S. Cl.
CPC ............. G16H 20/10 (2018.01); G16H 10/60 (2018.01)
(58) Field of Classification Search
None
See application file for complete search history.

(56) References Cited

U.S. PATENT DOCUMENTS

| | | | | |
|---|---|---|---|---|
| 9,147,163 B1 * | 9/2015 | Nease | ..................... | G16H 40/60 |
| 2002/0095424 A1 * | 7/2002 | Chung | ................... | G16H 10/60 |
| 2014/0074509 A1 * | 3/2014 | Amarasingham | ...... | G16H 50/70 705/3 |
| 2017/0300656 A1 * | 10/2017 | Cox | ....................... | G16H 50/20 |

OTHER PUBLICATIONS

Miles et al. ("Using machine-learning risk prediction models to triage the acuity of undifferentiated patients entering the emergency care system: a systematic review." Diagnostic and prognostic research. 4 (2020): 1-12) (Year: 2020).*

* cited by examiner

*Primary Examiner* — Christopher B Tokarczyk
(74) *Attorney, Agent, or Firm* — Nixon & Vanderhye PC

(57) ABSTRACT

The technology described herein is related to, among other aspects, a system that optimizes the timing component associated with targeted interventions while minimizing "member abrasion." The technology further relates to implementing a dynamic learning model that adapts to individual member behavior and can leverage more sophisticated fill patterns and peak receptivity to engage a member at a moment most likely to create a desired fill behavior. The technology further relates to an improved user interface for conveying such intervention information and data.

20 Claims, 12 Drawing Sheets

500

501 — Obtain & Process Claims Data

502 — Determine Group For Patient(s)

503 — Prioritize Patient(s) Based on Grouping

504 — Modify Listing in Accordance with Intervention Type

505 — Generate Output Data

| Field | Description/Notes | Example Row |
|---|---|---|
| Member ID | Unique member ID | 1234ABCD |
| Member First Name | | John |
| Member Last Name | | Smith |
| Member DOB | | 1/5/1940 |
| Member Sex | | M |
| Claim Number | Unique claim ID | 192433421999 |
| Claim Status | Indicates if paid, adjusted, reversed, or denied | Paid |
| Service Date or Fill Date | | 7/21/2016 |
| Rx Number | Prescription ID assigned by the pharmacy | 173-214 |
| Prescription Date | Date prescription was ordered by physician | 6/21/2016 |
| ProviderNPI | NPI of prescribing provider | 600003359 |
| PharmacyNPI | NPI of pharmacy | 500022488 |
| NDC Drug Code | | 52427044290 |
| Days Supply | | 30 |
| Metric Quantity | | 60 |
| Paid Date | | 7/21/2016 |
| Paid Amount | | $10 |
| Allowed Amount | | $20 |
| Copay Amount | | $10 |
| Coinsurance Amount | | $0 |
| Ingredient Amount | | $0 |
| Deductible Amount | | $0 |
| Dispensing Fee | | $0 |

| | Field | Description | Example |
|---|---|---|---|
| | patKey | Unique Key | 400000002 |
| 451 | memberid | Member Identier | 400000002 |
| | providerNPI | Provider National Provider Identifier | 600000605 |
| | providerId | Client Provider Id | AC3431 |
| | amtAllowed | Allowed Amount | 175 |
| | amtCapitation | Capitated Amount | 0 |
| | amtCharged | Charged Amount | 175 |
| | amtCob | Cordination Of Benefits Amount | 10 |
| 452 | amtCoinsurance | Coinsurance Amount | 50 |
| | amtCopay | Copay Amount | 25 |
| | amtDeductible | Deductible Amount | 75 |
| | amtPaid | Paid Amount | 15 |
| | amtWithhold | Withheld Amount | 0 |
| 453 | serviceDate | Service Date | 12/15/2018 |
| | paidDate | Paid Date | 1/25/2019 |
| 454 | claimNumber | Claim Number | 421932391 |
| 455 | claimNumberLine | Line Number | 1 |
| | claimsStatus | Claims Status | Paid |
| | diagnosisCode1 | Diagnosis Code1 | S20372A |
| | diagnosisCode2 | Diagnosis Code2 | R94 |
| 456 | diagnosisCode3 | Diagnosis Code3 | S56012 |
| | diagnosisCode4 | Diagnosis Code4 | S72441K |
| | diagnosisCode5 | Diagnosis Code5 | B302 |
| | procedure1 | Surgical Procedure Code1 | 0HR6X74 |
| | procedure2 | Surgical Procedure Code2 | 0R9V4ZZ |
| 457 | procedure3 | Surgical Procedure Code3 | 06164ZY |
| | procedure4 | Surgical Procedure Code4 | 041D0K3 |
| | procedure5 | Surgical Procedure Code5 | 0C5M3ZZ |
| | cptHcpcs | CPT or HCPCS Codes | 46600 |
| | cptmod1 | CPT modifier1 | C2 |
| | cptmod2 | CPT modifier2 | A3 |
| | revenueCode | Revenue Codes | 699 |
| | drg | Diagnosis-related group (DRG) Codes | 230 |
| | placeOfService | Place Of Service Code | 21 |
| 458 | serviceSetting | Service Setting | IP |
| | placeOfServiceCMS | CMS Place Of Service Code | 21 |
| | admissionDate | Admission Date | 12/15/2018 |
| 459 | dischargeDate | Discharge Date | 12/18/2018 |
| | lengthOfStay | Length Of Stay for Admissions | 4 |
| | billTypeCode | Type of Bill Code | 749 |
| | cptHcpcsCategory | CPT or HCPCS Category | surgery |
| | revenueERFlag | Revenue Code Emergency Room Flag | 0 |
| | revenueRoomBoardFlag | Revenue Code Room and Board Flag | 0 |
| | flagEsrd | Member in ESRD Flag | 0 |
| | flagHospice | Member in Hospice Flag | 0 |
| | flagSnf | Member in Skilled Nursing Facility Flag | 0 |
| | inpatient_outpatient_code | Inpatient or Outpatient Code | 1 |
| | units | Number of Units or Services | 3 |

MEDICATION ADHERENCE

CHOLESTEROL

⚠ HIGH RISK OF NON-ADHERENCE | LATE TO FILL — 631

OVERVIEW: Star Status: In Play | Index Date: 01-20-2020 | next Fill Due: 03-22-2020 (40 days late) | 90-Day Conversion Eligible

FILL DETAILS

| FILL DATE | MEDICATION | DAYS SUPPLY | QUANTITY DISPENSED | PRESCRIBER | PHARMACY | NEXT DUE |
|---|---|---|---|---|---|---|
| ∨ 02-21-2020 | Lovastatin Tab 20 MG | 30 | 30.00 | RONALD SMITH NPI: 600005000 | PHARMACY #1 NPI: 500090000 | 03-22-2020 |
| > 01-26-2020 | Atorvastatin Calcium Tab 40 MG (Base Equivalent) | 30 | 30.00 | RONALD SMITH | PHARMACY #1 | 02-25-2020 |

DIABETES

LOW RISK OF NON-ADHERENCE | PROACTIVE OUTREACH — 632

OVERVIEW: Star Status: In Play | Index Date: 01-26-2020 | Next Fill Due: 05-13-2020 (Due in 12 days) | 90-Day Conversion Eligible

FILL DETAILS

| FILL DATE | MEDICATION | DAYS SUPPLY | QUANTITY DISPENSED | PRESCRIBER | PHARMACY | NEXT DUE |
|---|---|---|---|---|---|---|
| ∨ 04-13-2020 | Metformin HCl Tab ER 24HR 500 MG | 30 | 120.00 | RONALD SMITH NPI: 600005000 | PHARMACY #1 NPI: 500090000 | 05-13-2020 |
| > 01-26-2020 | Metformin HCl Tab ER 24HR 500 MG | 30 | 120.00 | TARA JOHNSON | PHARMACY #2 | 02-25-2020 |

BLOOD PRESSURE

⚠ MODERATE RISK OF NON-ADHERENCE | READY TO FILL

OVERVIEW: Star Status: In Play | Index Date: 01-26-2020 | Next Fill Due: 05-13-2020 (Due in 12 days) | 90-Day Conversion Eligible

SYSTEMS AND METHODS FOR GENERATING USER INTERFACE DATA ASSOCIATED WITH ADHERENCE INTERVENTION DATA

CROSS REFERENCE TO RELATED APPLICATION(S)

This application claims priority to U.S. Patent Application No. 63/138,115, filed Jan. 15, 2021, the entire contents of which are incorporated herein by reference.

BACKGROUND AND SUMMARY

Patients around the world are prescribed medications for a variety of different reasons that can include their personal health and benefit. In many instances, patients may have recurring medications that require refills. Sometimes these refills are on an as needed basis (e.g., member does not need to take medication daily) where other refills may be recurring consistently (e.g., monthly).

While it may benefit most patients to timely refill their prescriptions (e.g., fill before they have run out of medication), many times patients do not timely refill. Reasons for not refilling a prescription could be intentional (e.g., patient decides they no longer need the medication) or unintentional (e.g., patient forgets to refill the medication). Missing refills for certain medications could result in adverse health effects for the patient which could lead to increasing health care costs for both the patient as well as a medical provider (e.g., insurance company).

Certain technologies exist for ensuring patients are adherent to a particular medication (also referred to as a therapy). Some example technologies are discussed in, at least, U.S. patent application Ser. Nos. 13/729,817, 15/928,763, and 16/918,517, each of which are incorporated herein by reference. The technologies described in these applications can provide an analytic approach that improves medication adherence as well as calculating and identifying which patients have the most value in targeted intervention.

The conventional technology is useful to identify patients that require targeted intervention to adhere to a particular therapy. However, the conventional technology could benefit from a more refined method for carrying out interventions as well as an improved tool for conveying such information to an end user. The technology described herein is related to, among other aspects, a system that optimizes the timing component associated with targeted interventions while minimizing "member abrasion" (e.g., member displeasure due to being targeted too frequently). The technology further relates to implementing a dynamic learning model that adapts to individual member behavior and can leverage more sophisticated fill patterns and peak receptivity to engage a member at a moment most likely to create a desired fill behavior. The technology further relates to an improved user interface for conveying such intervention information and data.

Accordingly, it will be appreciated that new and improved techniques, systems, and processes are continually sought after.

Copyright Notice

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

BRIEF DESCRIPTION OF THE DRAWINGS

FIGS. 4A and 4B show non-limiting example data structures;

FIGS. 6A-D show non-limiting example user interfaces associated with the system.

DETAILED DESCRIPTION OF THE TECHNOLOGY

Selected Definitions

Figure 1A:
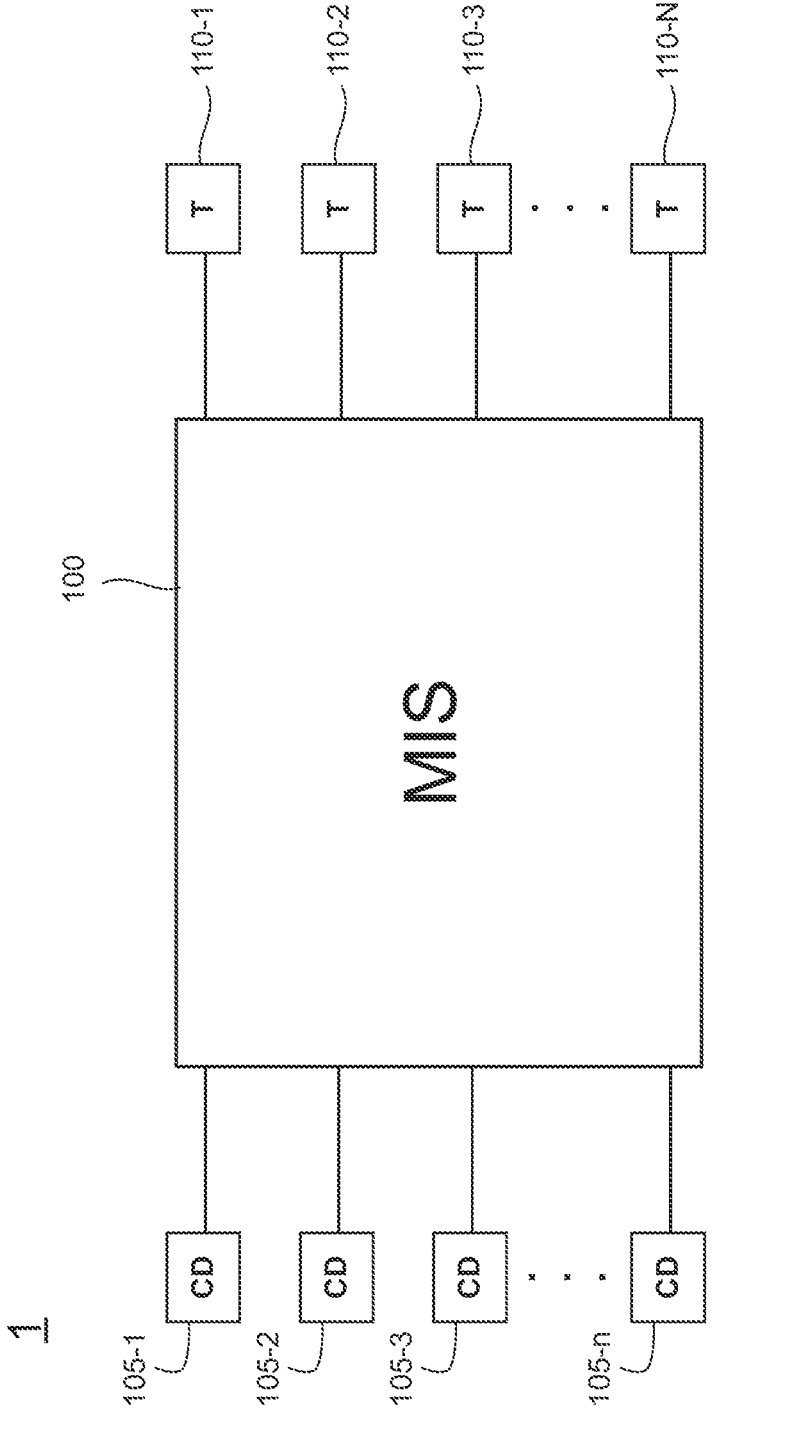
FIGS. 1A and 1B depict a non-limiting example block diagram of a system.

When it is described in this document that an action "may," "can," or "could" be performed, that a feature or component "may," "can," or "could" be included in or is applicable to a given context, that a given item "may," "can," or "could" possess a given attribute, or whenever any similar phrase involving the term "may," "can," or "could" is used, it should be understood that the given action, feature, component, attribute, etc. is present in at least one embodiment, though is not necessarily present in all embodiments.

As used in this document, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage.

As used in this document, the term "and/or" includes any and all combinations of one or more of the associated listed items.

In the following description, for purposes of explanation and non-limitation, specific details are set forth, such as particular nodes, functional entities, techniques, protocols, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail.

Overview

The technology described herein relates to, among other topics, a system for advanced intervention targeting for different members and different therapies of interest. The technology includes underlying patient selection (e.g., targeting) analytics and further includes an improved user interface that conveys tangible reasons for a health plan member to be called (e.g., medication is ready to be refilled).

The technology includes a targeting method that can group members in a continuum of importance of intervention. The continuum of importance can range from necessity (e.g., out of drug, close to expiration) to proactive, and/or from no-benefit to potential "harm" in contacting the member. It should be appreciated that timing is a critical component and that one or more members can move across different groups over time (independent of refilling).

In a non-limiting example, the system can use claims data (e.g., medical claims data, pharmacy claims data) to identify the group numbers and provide a reason for intervention and outreach to a particular member (along with additional helpful information). The group numbers to which a patient may be assigned at a given point in time can be used to prioritize a listing of patients for recommending intervention. The system can provide such information via a user interface that improves the user's overall human-computer interaction with the system and further improves the prospect of member behavior.

Examples of at least three different fields are envisioned by the technology described herein. It should be appreciated that these fields can be associated with member assignment in a particular grouping (or a reason for why the member is in a particular grouping). A first field includes a timing component that relates to different timings in which a member may be associated with a particular group. The timing component can include, at least, therapy recommendation being early, therapy intervention is recommended to discuss with patient because they are able to pick up their medication(s) at a certain time, and/or therapy is recommended to discuss with patient because they are currently late to pick up their medication(s). The patient may be placed in a particular grouping where the timing component is associated with the grouping.

A second field can correspond to a risk component associated with the patient. The risk component can be based on the history associated with a patient (e.g., patient fill history) over a period of time (e.g., calendar year). The risk component can include a spectrum as to how much risk is associated with medication adherence for one or more medications. The risk component can include, at least, therapy being low risk of non-adherence for the year, therapy being moderate risk of non-adherence for the year, and/or therapy being high risk of non-adherence for the year. As noted above, the risk component can also be used in determining which grouping to place a member (or for explaining why a member is in an associated group). A non-limiting example table is provided below that shows a listing of group numbers and an associated description for each group corresponding to the respective group number:

| Group | Description |
| --- | --- |
| 1 | High risk and late in fill |
| 2 | High risk and early in fill |
| 3 | Medium risk and late in fill |
| 4 | Low risk |
| 5 | Potential harm of contacting member due to timing |
| . . . | . . . |
| N | Ineligible |

In one non-limiting example embodiment, the timing component and the risk component may be used to determine (or explain) a group selection for a member (e.g., at a given point in time). For example, a member that may be late to fill in a given fill cycle (e.g., timing component) and has a high risk of non-adherence (e.g., risk component) may be associated with group 1. Likewise, a member that is in the middle of a given fill cycle and has a low risk of non-adherence may be associated with group 4. Depending upon the identified group, the member may be prioritized accordingly for recommending an intervention. For example, a member in group 4 may be "lower priority" for recommending an intervention compared to a member in groups 1-3. It should be appreciated that the type of intervention may also be factored into the prioritization of the member. That is, and as discussed herein, the technology not only improves timing associated with recommending an intervention but takes into account "member abrasion." For example, a member may be associated with group 5 because they are likely to receive an intervention soon and at a better time (e.g., ready to refill medication), thus limiting unnecessary interaction with a member that could reduce member likelihood of responding to intervention. Additionally, some interventions may be considered as being more abrasive (e.g., telephone call, in-person visit) while other interventions may be considered less abrasive (e.g., text message, email, push notification). Thus, the technology can also take into account the type of intervention when prioritizing a patient for recommending intervention.

A third field can correspond to supplemental information. The supplemental information can include, at least, a member filling at multiple pharmacies and/or a member being new to a health plan. The supplemental information can be used to help identify or explain why the patient is in a particular grouping. For example, a member being new to a health plan may indicate that an early intervention to touch base and discuss the member's medication(s) would be preferred. The supplemental information (i.e., from the third field) can be used in addition to the first and second fields to help explain why a member may be associated with a specific grouping.

As a non-limiting example, and as discussed herein, the groupings assigned to a given member may be based on individual therapies. However, it should be appreciated that a member may be on multiple therapies and that a given grouping can be assigned based on the multiple therapies. That is, members may be on multiple therapies and the group a member falls into for one therapy may outweigh the group for another. For example, if a member is in group 1 for one therapy and group 4 for another, the member may be placed in group 1 as at least one therapy is a high priority. On the other hand, if one therapy is group 4 and another is group 5, the potential harm of group 5 may outweigh the low risk of group 4. These examples are of course non-limiting and the technology described herein envisions any variety of methods for assigning a group to a member.

Compared to conventional techniques, the technology described herein can improve the timing at which to carry out an intervention. It should be appreciated that during a given fill cycle for a medication, the user can fall within at least one of three windows that include a "proactive" window, a "fill eligible" window, and a "out of drug" window. The conventional approach may prioritize patients for a certain timing that may not be as useful given the point in time the patient is within the fill cycle.

The technology described herein advantageously improves the timing for recommending an intervention. It should be appreciated that the technology can improve (or put a "premium" on) the timing of an intervention (e.g., call) while limiting "member abrasion," where more interventions are made (e.g., increased intensity) as needed thereby improving performance. That is, the technology can improve the timing for recommending an intervention so that more useful recommendations are made within a particular window of a fill cycle (e.g., optimize days missed while taking into account member abrasion). The technology can provide a dynamic "learning" system that minimizes recommendations where members may be monitored after an intervention to determine pattern breaks (or whether further intervention is required). The reason for the intervention is transparent (e.g., easily explained) and virtually all members non-adherent at the end of a given year will have been highly prioritized and likely received intervention (assumes provider is conducting interventions at a sufficient amount).

It should be further appreciated that the technology provides an improved user interface for conveying such information to one or more end users. In particular, the technology provides a user interface having various graphical and interactive elements associated with medication adherence as well as intervention recommendations associated with the groupings described herein, among other aspects. The user interface thus improves the overall human-computer interaction and provides an easy-to-use mechanism for an end user to understand highly complicated information.

Figure 1B:
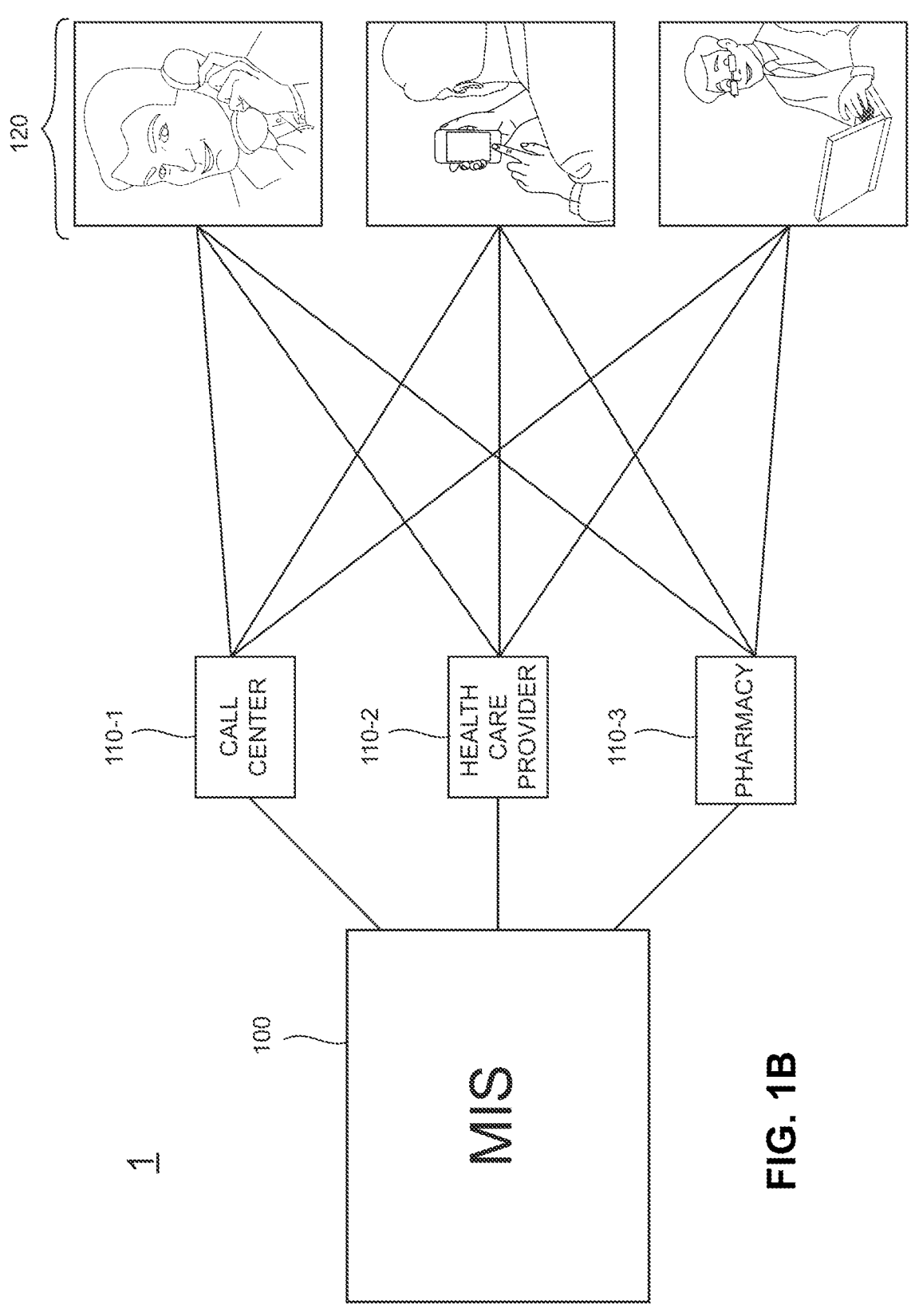
Figure 2:
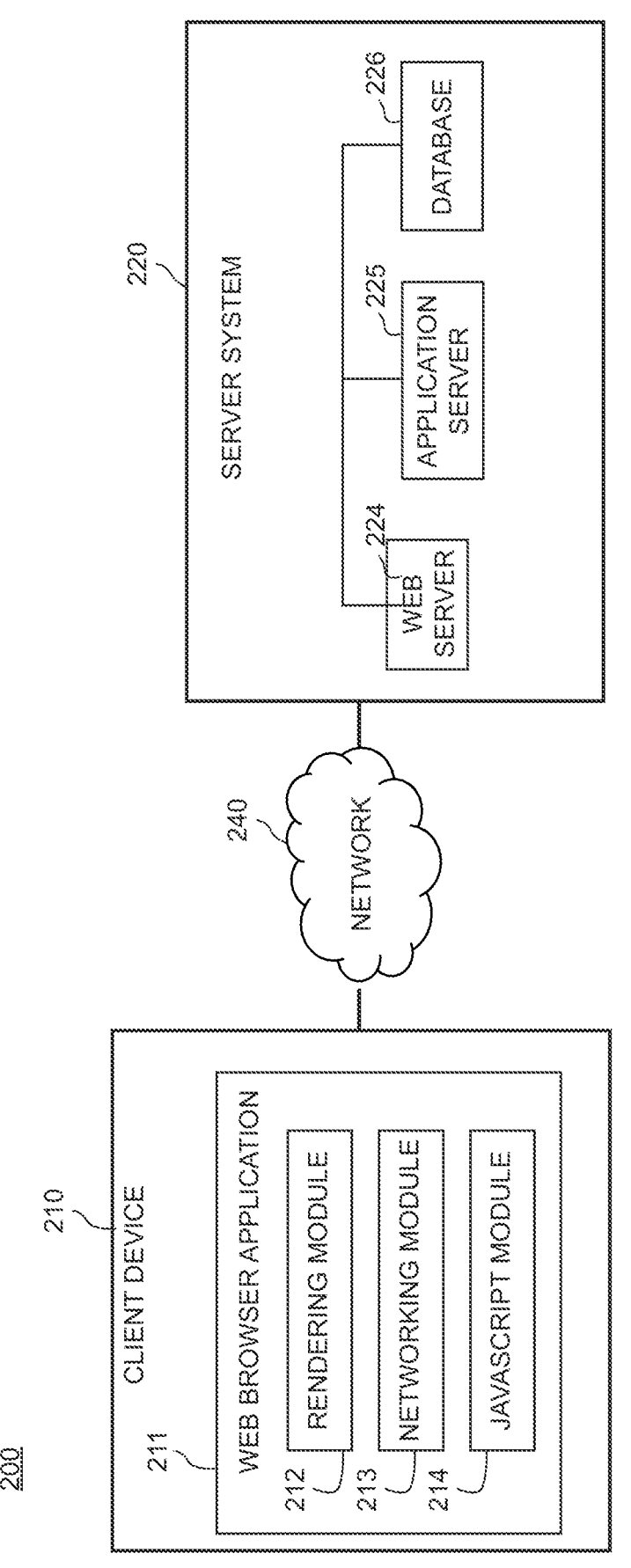
FIG. 2 depicts a non-limiting example block diagram of software components included in the exemplary system.
Figure 3:
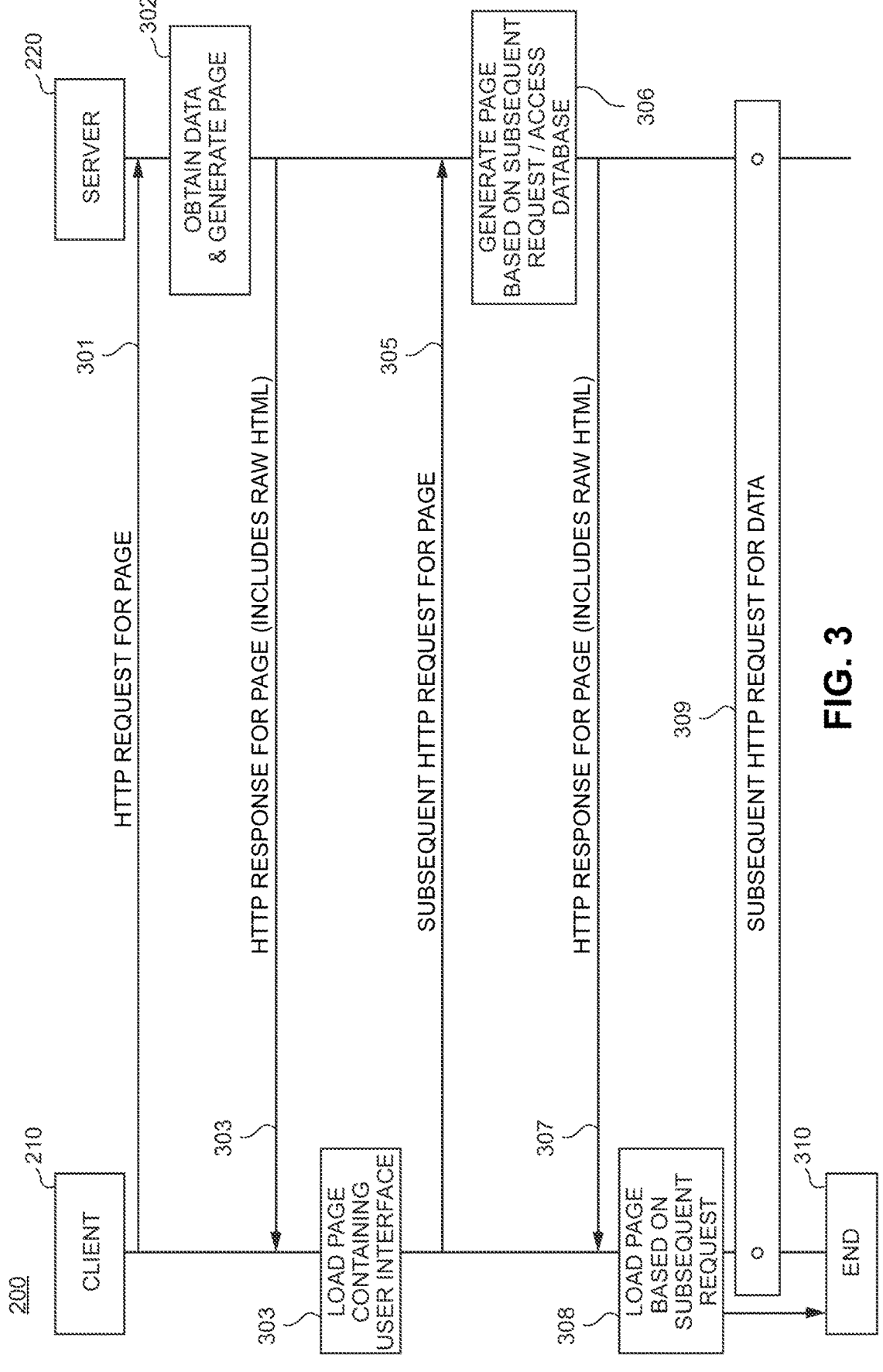
FIG. 3 shows a non-limiting communication process between a client and server in an exemplary system according to the present technology.
Figure 5:
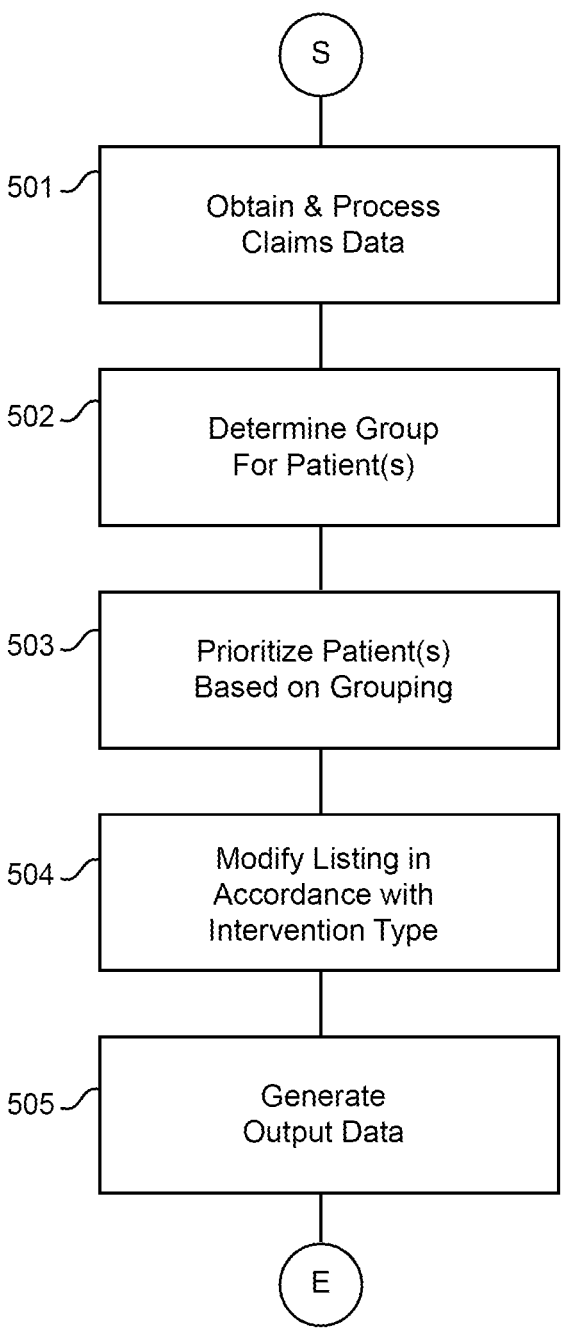
FIG. 5 shows a non-limiting example flowchart depicting processes carried out in association with the system.

FIGS. 1A and 1B depict a non-limiting example block diagram of a system. FIG. 2 depicts a non-limiting example block diagram of software components included in the exemplary system, and FIG. 3 shows a non-limiting communication process between client device(s) 210 and server system(s) 220 in the system 200. FIGS. 4A and 4B show non-limiting example data structures. FIG. 5 shows a non-limiting example flowchart depicting processes carried out by the system. FIGS. 6A-D show non-limiting example user interfaces associated with the system, and FIG. 7 shows a non-limiting example block diagram of hardware components comprising the system shown in FIG. 2

In many places in this document, software modules and actions performed by software modules are described. This is done for ease of description; it should be understood that, whenever it is described in this document that a software module performs any action, the action is in actuality performed by underlying hardware components (such as a processor and a memory) according to the instructions and data that comprise the software module.

FIG. 1A shows a non-limiting example diagram of a system 1 in which data related to, at least, medication intervention information is conveyed to several endpoints. In one example, a medication intervention system 100 can communicate information to one or more terminal devices 110-1-110-n and can also receive data from one or more terminal devices 105-1-105-n. For example, the medication intervention system can receive data packets from terminal devices 105-1-105-n and send data packets to the terminal devices 110-1-110-n that include information for providing interventions.

In one example, the system 100 will use processing resources of the system to provide data associated with patient adherence to one or more medications and/or medical therapies. Terminal devices 105-1-105-n can also transmit data packets including information related to claims data (which can include, at least, medical claims data and/or pharmacy claims data) to system 100. For example, device 105-1-105-n can transmit data packets (or data files) used to form data structures that provide claims data (as described in further detail herein). The system 100 can use the data transmitted from devices 105-1-105-n in order to generate recommendations for interventions.

The system 100 can communicate data packets that convey information related to interventions to devices 110-1-110-n. For example, system 100 can use claims data received from devices 105-1-105-n to, among other aspects, generate recommendations for interventions and then transmit data packets carrying this information to devices 110-1-110-n. Terminal devices 110-1-110-n can use the transmitted data to generate user interfaces, web pages, and any other variety of graphical user displays that can convey information to one or more users of the terminal devices 110-1-110-n.

It should be appreciated that the system 100 can communicate with devices 105-1-105-n and 110-1-110-n using a variety of methods. In one example, the system 100 will be in data communication with the devices using network interface components that allow the system 100 to communicate over a network (e.g., the internet).

FIG. 1B shows a non-limiting example diagram of the system 100 when communicating adherence and intervention data to different entities associated with devices 110-1-110-n. In the example shown in FIG. 1B, the system 100 may have received claims data from one or more claims data sources via terminals 105-1-105-n (shown in FIG. 1A) and then utilize the claims data to generate adherence and intervention data associated with a plurality of patients.

In one non-limiting example, the entities associated with terminals 110-1-110-n can be parties that facilitate the overall health care of the patient to improve their adherence to one or more medications of interest. For example, the entities can include a call center, a health care provider (e.g., an insurance company, physician's office), and/or a pharmacy, among others. The system 100 could generate medication adherence and intervention data and transmit the same to terminals associated with each of the entities, where the entities can then use the data to reach out to different patients 200.

The patients 200 could experience outreach using a variety of different methods including, but not limited to, live telephone calls, automated telephone messages, voicemails, email messages, SMS messages, MMS messages, push notifications, physical mail, and/or out- (or in-) patient outreach. The system 100 may generate a list of patients (e.g., ranked based on a need for intervention), medications associated with each patient, and one or more interventions for each patient to ensure they are adherent with the particular medication, and communicate such data to terminals 110-1-110-n associated with each of these entities.

Using the call center (having terminal 110-1 in the example of FIG. 1B) as an example, system 100 may generate a list of patients that can be communicated to terminal 110-1 via a data file or a user interface generated at the terminal 110-1. The call center may use this information to conduct outreach to one or more patients on the list. In some cases, the outreach may be in the form of a human calling (or possibly visiting) the patient to attempt to have the patient adhere to a medication of interest (e.g., by properly using the medication and/or filling the medication). In other instances, the call center may use data services to conduct the outreach (e.g., via automated telephone call, email message, push notification).

In one example, the system 100 will use processing resources to provide data associated with interventions for one or more patients. Data sources 105 can also transmit data packets including information related to medical and/or pharmacy claims data to system 100. For example, data sources 105 could comprise terminal devices that can transmit data packets (or data files) used to form data structures that provide claims data. It should be appreciated that throughout this document, the system is described as communicating claims data which can include both the medical claims (e.g., doctor visits, hospital visits) and pharmacy claims (e.g., claims for prescription medications). That is, the term "claims data" may refer to an actual medical claim, a pharmacy claim, or both. Data sources 105 may also transmit data related to lists of medications for one or more patients. The system 100 can use the data transmitted from data sources 105 in order to generate information related to intervention support.

The system 100 can communicate data packets that convey information related to intervention support to terminal devices 110. For example, system 100 can use claims data received from data sources 105 to, among other aspects, generate user interface data related to patient(s) medication usage and then transmit data packets carrying this information to devices 110. Terminal devices 110 can use the transmitted data to generate user interfaces, web pages, and any other variety of graphical user displays that can convey information to one or more users of the terminal devices 110.

It should be appreciated that the system 100 can communicate with devices 105 and 110 using a variety of methods. In one example, the system 100 will be in data communication with the devices using network interface components that allow the system 100 to communicate over a network (e.g., the internet).

FIG. 2 shows a non-limiting example diagram of a system 200 wherein the application architecture may be implemented. As will be described below, one or more web applications defined according to the application architecture can be deployed in the system 200, and the various components in the system 200 (such as the client system 210 and server system 220) can perform different functions related to the deployed web applications. As will be discussed below, FIG. 2 shows primarily software modules (such as the web browser application 211) that run at the client system 210 and server system 220; details regarding example hardware components that may be used to execute these software modules are provided below with reference to FIG. 7, as well as in other places in this document.

In the example shown in FIG. 2, the client system 210 can communicate with a server system 220 (e.g., via a network 240). It should be appreciated that the network 240 could comprise a network of interconnected computing devices, such as the Internet. The network 240 could also comprise a local area network (LAN) or could comprise a peer-to-peer connection between the client system 210 and the server system 220.

The server system 220 can include a web server 224 that performs functionality such as implementing the HTTP protocol and communicating with the web browser application 211 (described in further detail below) in the client system 210 via HTTP. The server system 220 can also include an application server 225 that can, for example, execute server-side (or "back end") instructions for applications implemented according to the architecture. The server system 220 can also include a database 226 that manages the persistent storage of data that is used at the server system 220. The database 226 may be or include one or more of: a relational database management system (RDBMS); an object-oriented database management system (OODBMS); an object-relational database management system (ORDBMS); a not-only structured query language (NoSQL) data store; an object cache; a distributed file system; a data cluster (based on technology such as Hadoop); and/or any other appropriate type of data storage system.

The client system 210 can include software components for performing processing related to applications defined according to the described system. As a non-limiting example, the client system 210 may have a web browser application 211 consisting of, at least, a rendering module 212, a networking module 213 and a JavaScript module 214. Of course, these modules are a non-limiting example, and the application 211 can comprise several more modules and/or different modules than those shown in FIG. 2.

The rendering module 212 can implement functionality for the graphical display and rendering of web page user interfaces. It can, for example, generate graphical data that corresponds to the HTML and/or DOM that defines a web page processed by the web browser application 211; this graphical data can, potentially after further modification/transformation by the operating system of the client system 210, be displayed on a display of the client system 210. Alternatively or additionally, whenever it is described in this document that the client system 210 renders/displays a web page, the rendering/displaying module 212 may perform functionality related to the rendering/display of the web page.

The networking module 213 can implement the HTTP protocol, and be used to handle various HTTP messages between the client system 210 and the web server 204 in the server system 200. Alternatively or additionally, whenever it is described in this document that the client system 210 communicates using HTTP, the networking module 213 may handle the HTTP aspects of such communications.

The JavaScript module 214 can be used to execute JavaScript scripts, manipulate JavaScript objects, modify the DOMs of web pages loaded at the web browser application 211, and perform other functionality related to JavaScript. The JavaScript module may be, for example, a JavaScript engine, a JavaScript virtual machine, a JavaScript runtime, or any other type of software module capable of executing JavaScript instructions. Alternatively or additionally, whenever it is described in this document that the client system 210 performs functionality related to JavaScript, such functionality may be handled by the JavaScript module 214.

It should be appreciated that while the diagram in FIG. 2 shows the components existing within a single system, the components could be incorporated in multiple systems and/or a distributed computing environment (e.g., a cloud computing environment). Thus, the processing system 200 is not limited to a single component and can be incorporated into multiple components.

FIG. 3 shows a non-limiting communication process between client device(s) 210 and server system(s) 220 in the system 200. FIG. 3 relates to an example timing diagram for obtaining data and generating an example user interface that uses the described interface generated in the system. In this example, and as will be described in detail below, the content for at least one page within the application is loaded at the client device 210. Although not shown in FIG. 3, the client device 210 may run the web browser application 211 shown in FIG. 2 and described above, and the server system 200 may run software modules such as the web server 204, application server 205, and database 206 shown in FIG. 2 and described above. It should be appreciated that the processes shown in FIG. 3 depict communication between the server system 220 and multiple client devices 210. Though this example is non-limiting and the technology envisions any variety of client devices 210 and/or server systems 220 carrying out the communication process shown in FIG. 3

It should be appreciated that the client device(s) 210 and server system(s) 220 are shown as single components. However, client device(s) 210 and server system(s) 220 may be multiple components (e.g., different and/or distributed devices). For example, client device(s) 210 may be a first entity in certain actions shown in FIG. 3, but may be a second entity (different from the first entity) for other actions shown in FIG. 3.

At action 301, the client device 210 sends a data message containing one or more elements that include, at least, claims data. The data messages can contain information related to claims data (e.g., pharmacy claims data, medical claims data, enrollment data). In one example embodiment, the data message can be communicated as a flat file having a data structure as shown in further detail in FIGS. 4A and 4B. The system 100 could receive the flat file via a file transfer protocol (FTP) site and the file could provide the data elements as a pipe delimited file (or a comma separate file). This example is of course non-limiting and the file could provide the data elements in an XML format or any other variety of formats capable of presenting a data structure.

It should also be appreciated that the technology envisions a variety of methods for receiving/obtaining the data messages from the endpoint devices and are thus not limited to receiving a flat file. The data messages may also be obtained by the system 100 from the client devices in a batch mode at fixed times during a given day. Of course, the timing for receiving the data messages is non-limiting and the technology envisions a variety of timings for receiving the messages including real-time transfer of the data message. It should also be appreciated that server 220 may send an acknowledgement message to client 210 acknowledging receipt of the data message.

At action 302, the server 220 parses the data message in order to extract one or more elements of data. As shown in FIGS. 4A and 4B, the exemplary data message could include several rows and columns corresponding to different data types and their associated data elements. For example, one column could include a "Field" designation having elements related to different fields in a database entry. The server 220 can parse the data message to extract elements in each "Field" and the corresponding information associated with the field (e.g., a description or notes of the field).

Upon parsing the data message, the server 220 can store the elements from the parsed data message into a database. As a non-limiting example, the database could reside in server system 1250 (e.g., in memory 1254) as shown in FIG. 7. This example is non-limiting and the technology envisions a variety of methods for storing the database including, but not limited to, storing the database across multiple memories in the system 1250 and/or storing the database in a distributed (e.g., cloud) computing system.

At action 303, a client device 210 can transmit list data containing a list of one or more medications for which a patient may receive a prescription. The list data can include a listing of medications for which the patient is currently taking and/or a listing of medications for which the patient is being proposed to take, and the list can be prioritized based on member grouping, as discussed herein. At action 304 the server 220 can process the data in the list and determine if the list should be modified (e.g., adding medications, removing medications, modifying proposed medications), and/or if certain intervention recommendations should be generated.

At action 305, the client device 210 sends an HTTP request message that includes a URL that points to a web page. At action 306, the server system 220 obtains, at least, the data from database 206 containing portions of the medication management data. The server system 220 can also obtain other information for generating the web page. For example, the server system 220 will obtain information used in different portions of the page, such as the header and footer, as well as other elements that could populate the body of the page.

At action 307, the server system 220 begins preparing an HTTP response message to send back to the client device 210. In preparing the response, the server system 220 generates code for rendering a web page on the client device 210. The code can contain at least the data related to the medication management, as well as the additional content comprising the page requested by the client device 210. The server system 220 can then send an HTTP response message for the page; this response may include HTML code, JavaScript modules (including AngularJS modules) and Javascript code, and other code that corresponds to the page.

At action 308, the client device 210 can then fetch the code for rendering the web page from the server system 220 and then render the page using the web browser application 211. More specifically, the web browser application will load various elements using the rendering module 212 and different Javascript objects using the Javascript module 214.

In certain implementations, the client 210 may make additional requests to the server system 220 to obtain more information for generating a particular page (or for generating other aspects/portions of the page). For example, the user may select an object on the page where the client device 210 may need additional data so that it can modify the rendered page based on the user selection, or the user may make a selection requiring the client device 210 to load a new page. At action 309, the client device 210 can make such a subsequent request to server system 220 in which server system 220 will produce the code for rendering a new/modified page at client device 210.

The client device 210 and server system 220 can initiate further subsequent HTTP requests for data in which the processes described with respect to at least actions 305-309 can be repeated. Although action 301-302, 303-304, and 305-309 are shown in FIG. 3 as occurring once, these actions 301-302, 303-304, and 305-309 may, in various embodiments, be repeated a number of times during the loading of a particular page.

FIGS. 4A and 4B show non-limiting examples of data structures 400 and 450 communicated between devices within the system 1. In one example embodiment, the data structure 400 could include data elements related to pharmacy claims data as part of a pharmacy claims data message while data structure 450 could include data elements related to medical claims data as part of a medical claims data message. This example is of course non-limiting and the technology described herein envisions any variety of data that could be included in the exemplary data structures 400 and 450.

The example data structure 400 shown in FIG. 4A may be communicated as a data message having one or more rows and/or columns comprising the specific data elements. In the example shown in FIG. 4A, the data structure 400 has at least three columns indicative of three different types of data elements. For example, the data structure 400 contains a field column 410, a description/notes column 420, and an example row column 430. Each of these columns can be indicative of an associated data type related to each data element in the column. For example, field column 410 contains data elements associated with database fields defined for particular rows where description/notes column 420 and example row column 430 provide corresponding elements associated with each item in field column 410. It should be appreciated that the example shown in FIG. 4A is non-limiting and that data structure 400 may contain any variety of columns and/or rows including, but not limited to, a type column indicating the data type for a particular row (e.g., character/string, numeral, date, general, time, percentage, fraction, scientific, currency, custom) and/or a length indicating the data length for a particular row (e.g., 50 characters, "MM/DD/YYYY" specified date format, a numeral value of maximum amount).

In one non-limiting example, field column 410 could contain several data elements associated with database fields for a pharmacy claims data record. In particular, the field column 410 could contain items that comprise information associated with the claims data record that can identify the individual as well as the pharmacy claims data associated with the individual. For example, the data structure 400 could contain a row of items for a particular member ID 401, claim number 402, claim status 403, service or fill date 404, Rx number 405, prescription date 406, paid date 407, days supply 408, metric quantity 409, and/or NDC drug code 411. As can be seen in FIG. 4A, this list of items is only an example and the data structure 400 envisions a variety of other data items.

The member ID 401 could correspond to a specific identification number for a patient/member of the system. In the example shown in FIG. 4A, member ID 401 has a corresponding description of "Unique member ID" in the description/notes column 420 as well as an identifier "1234ABCD" in the example row column 430. Claim number 402 could contain information correspond to a specific claim identification number (in this example, shown as "192433421999"). The claim number 402 could correspond to a unique identifier for an open pharmacy claim such as a prescription drug being purchased by the individual and processed by the individual's health insurance company. The claim status 403 could provide an indication as to the actual status of the claim (e.g., whether the claim is paid, adjusted, reversed, or denied). In the example shown in FIG. 4A, the claims status 403 of this particular claim is marked as "paid."

The data element for service or fill date 404 could correspond to when the particular prescription associated with the claim was filled (or when a medical service associated with the claim was performed). In this example, the service/fill date is "Jul. 21, 2016." The data structure 400 could also include a data item for a prescription number 405 corresponding to a prescription/drug identifier assigned by a particular pharmacy (in this case, "173-214"), and the prescription date 406 could correspond to the date the prescription was ordered by a physician (e.g., "Jun. 21, 2016"). Likewise, the paid date 407 could correspond to when the member/patient paid for the prescription (e.g., "Jul. 21, 2016").

The data element for days supply 408 could correspond to how many days supply the user was prescribed a particular medication where the metric quantity 409 may correspond to the actual amount (e.g., within the days supply 408 time frame). For example, the patient may be prescribed a medication for a period of 30 days (e.g., days supply 408) where the patient is to take the medication twice each day thus resulting in an amount of 60 units (e.g., metric quantity 409) for the medication.

The data element for NDC drug code 411 could correspond to the National Drug Code directory identifier for a medication. In the example of FIG. 4A, the NDC drug code 411 includes the identifier "52427044290" and could be used to identify a specific drug from the National Drug Code directory. It should be appreciated that some of the items within data structure 400 can be used to help identify patients that require a type of intervention. For example, system 1 can use the NDC drug code 411 to determine which patients are on a specific medication and then use information from data structure 400 (e.g., service date of fill date 404, member ID 401, prescription date 406, and/or days supply 408) to determine which group the patient should be placed in order to determine when intervention is appropriate.

It should be appreciated that these identified elements are non-limiting and the technology envisions a variety of any types and formats of data encapsulated in each data file. It should be appreciated that the example shown in FIG. 4A depicts each element as a string where each specific element could be converted to some other data type (e.g., by a sending or receiving device). For example, the device receiving the data message containing the data structure 400 could convert any of the elements to a whole number, an integer, a real number, a currency, a date and/or time, and/or a Boolean value. As explained above, the data message containing the data structure 400 could be sent as a flat file that could be of the form of a comma separated file, an XML file, and/or a tab delimited file. Of course, this example is non-limiting and the technology described herein envisions a variety of methods for transmitting/receiving such data.

The example data structure 450 shown in FIG. 4B may be communicated as a data message having one or more rows and/or columns comprising the specific data elements. In the example shown in FIG. 4B, the data structure 450 has at least three columns indicative of three different types of data elements. For example, the data structure 450 contains a field column 460, a description/notes column 470, and an example row column 480. Each of these columns can be indicative of an associated data type related to each data element in the column. For example, field column 460 contains data elements associated with database fields defined for particular rows where description/notes column 470 and example row column 480 provide corresponding elements associated with each item in field column 460. It should be appreciated that the example shown in FIG. 4B is non-limiting and that data structure 450 may contain any variety of columns and/or rows including, but not limited to, a type column indicating the data type for a particular row (e.g., character/string, numeral, date, general, time, percentage, fraction, scientific, currency, custom) and/or a length indicating the data length for a particular row (e.g., 50 characters, "MM/DD/YYYY" specified date format, a numeral value of maximum amount).

Data structure 450 could contain a variety of data elements in field column 460 that are used to populate a claims data record. For example, field column 460 could include a "patKey" corresponding to a unique key value, a "provider NPI" corresponding to a Provider National Provider Identifier, a "providerId" corresponding to a client provider ID, a "cptHcpcs" corresponding to corresponding to a Current Procedural Terminology (CPT) or Healthcare Common Procedure Coding System (HCPCS) codes, and/or "cptmod1" and "cptmod2" corresponding to CPT modifiers 1 and 2

(additional CPT modifiers can be sent/provided). Field column 460 may further include a "revenueCode" corresponding to one or more revenue codes (which may only be populated for in-patient and/or emergency room claims), a "drg" field corresponding to diagnosis-related group (DRG) codes, a "placeOfService" field corresponding to a place of service code (e.g., client value or CMS), a "placeOfService-CMS" corresponding to a CMS place of service code, a "billTypeCode" corresponding to a type of bill code, and/or a "cptHcpcsCategory" corresponding to a CPT or HCPCS category. Field column 460 may further include a "revenueERFlag" corresponding to a revenue code emergency room flag, a "revenueRoomBoardFlag" corresponding to a revenue code room and board flag, a "flagEsrd" corresponding to a member in ESRD flag, a "flagHospice" corresponding to a member in hospice flag, a "flagSnf" corresponding to a member in skilled nursing facility flag, an "inpatient_outpatient_code" corresponding to an Inpatient or Outpatient code, and/or a "units" field corresponding to a number of units or services. These examples are of course non-limiting and the data structure 450 may include any additional fields (or may exclude certain fields)

In further detail, field column 460 may include a memberID 451 field corresponding to an identification value for a particular member. In the example shown in FIG. 4B, memberID 451 could contain value "400000002" corresponding to a specific identifier of a particular member/patient identified in the pharmacy claim data record. The memberID 451 may be a unique value for each individual member and can uniquely identify other aspects associated with the memberID 451 by using the memberID 451 in a corresponding look-up table (e.g., for providing name, age, residence information).

Field column 460 may also include several amount 452 fields corresponding to different dollar amounts associated with a claim. In one non-limiting example, amount 452 fields could include an "amtAllowed" corresponding to an allowed amount for a particular claim, an "amtCaptitation" field corresponding to a capitated amount, and an "amtCharged" field corresponding to a charged amount for the claim. The amount 452 fields may further include fields related to an apportionment of benefits associated with a claim including, but not limited to, an "amtCob" field corresponding to a coordination of benefits amount, an "amtCoinsurance" field corresponding to a coinsurance amount, an "amtCopay" corresponding to a copay amount for a particular claim, an "amtPaid" field corresponding to a paid amount for the claim, and/or an "amtWithhold" field corresponding to a withheld amount for the claim. In one non-limiting example, these fields could relate to the different amounts associated with an overall payout for a claim.

The field column 460 may also include a serviceDate 453 related to a date a particular service was performed (e.g., when a medical service was performed) and may also include a "paidDate" corresponding to a date when a claim was paid. Field column 460 may also include a claimNumber 454 field that specifically identifies a claim number. For example, claimNumber 454 may include a numerical identifier (e.g., "421932391") that specifically identifies the claim in question where the claim may further include a "claimNumberLine" field corresponding to a particular line number for the claim. Field column 460 may further include a claimStatus 455 field indicating a status of a particular claim. In one non-limiting example, the claimStatus 455 field may indicate that a claim has been paid, denied, and/or reversed.

Field column 460 may further include diagnosis codes 456 fields corresponding to one or more diagnosis codes 456 for a patient/member. The example shown in FIG. 4B shows up to five diagnosis codes 456 for a member but this example is of course non-limiting and the technology described herein envisions any number of additional (or fewer) diagnosis codes 456. It should be appreciated that the diagnosis codes 456 may be used by the system 1 to identify certain disease conditions of a particular member.

Field column 460 may include additional fields related to surgical procedure codes 457 corresponding to one or more surgical procedures. The example shown in FIG. 4B shows up to five surgical procedure codes 457 for a member but this example is of course non-limiting and the technology described herein envisions any number of additional (or less) surgical procedure codes 457. The surgical procedure codes 457 may identify one or more procedures associated with a claim and may include specific procedures related to addressing a specific condition. For example, surgical procedure codes 457 may identify an endoscopy procedure which could be used in association with a patient having certain gastrointestinal issues. It may also be appreciated that the surgical procedure codes 457 may only be populated for in-patient (IP) and/or emergency room (ER) claims.

Field column 460 may further include a serviceSetting 458 field corresponding to a particular setting of a medical service. For example, serviceSetting 458 may relate to an in-patient (IP) setting, an out-patient (OP) setting, and/or an emergency room/department (ER) setting. This list is of course non-limiting and the technology described herein envisions any variety of settings. In the example shown in FIG. 4B, the setting relates to an in-patient (IP) setting.

Field column 460 may further include stay date 459 fields associated with a patient's stay in a particular setting. For example, stay date 459 fields may include an "admissionDate" field corresponding to a date of admission for a particular patient. For example, a patient may have an "admissionDate" of Dec. 15, 2018 corresponding to when the patient was admitted to a hospital. The stay date 459 field may further include a "dischargeDate" field corresponding to a date of discharge in which the patient was discharged from a hospital/medical environment. In one example, the patient may have a "dischargeDate" of Dec. 18, 2018 indicating that they left (i.e., were discharged) from the hospital on that particular date. Stay date 459 field may further include a "lengthOfStay" field indicating the overall length of a medical visit. Using the example above, "lengthOfStay" field is shown having a value "4" indicating that four days have passed since admission to discharge (i.e., December 15, 16, 17, and 18).

Many of the fields associated with field column 460 may be of a character/string type of individually defined lengths. However, and as mentioned above, certain fields may be of a different type. For example, amount 452 fields, "lengthOfStay," "revenueERFlag," "revenueRoomBoardFlag," "flagEsrd," "flagHospice," "flagSnf," and/or "units" fields may be of type "numeral." Likewise, "serviceDate," "paidDate," "admissionDate," and "dischargeDate" may be of "date" type represented in a particular date format (e.g., "MM/DD/YYYY").

It should be appreciated that these identified elements are non-limiting and the technology envisions a variety of any types and formats of data encapsulated in each data file. It should be further appreciated that the example shown in FIG. 4B depicts certain elements as a string where each specific element could be converted to some other data type (e.g., by a sending or receiving device). For example, the device receiving the data message containing the data structure 400 could convert any of the elements to a whole number, an integer, a real number, a currency, a date and/or time, and/or a Boolean value. As explained above, the data message containing the data structure 450 could be sent as a flat file that could be of the form of a comma separated file, an XML file, and/or a tab delimited file. Of course, this example is non-limiting and the technology described herein envisions a variety of methods for transmitting/receiving such data. It should be appreciated that the data extracted from the records shown in FIGS. 4A and 4B may be used alone, or in combination, to determine what grouping to place a particular patient for determining if and when to carry out an intervention.

FIG. 5 shows a non-limiting example process 500 carried out by system 1. FIG. 5 specifically shows a non-limiting example flowchart for compiling medical data for a patient and generating a resultant user interface. The process begins by system 1 obtaining and processing claims data (501). As mentioned above, the claims data could include both medical claims data (e.g., data structure 450) and/or pharmacy claims data (e.g., data structure 400). The system 1 may obtain data files including the claims data and then process the data files by parsing and extracting data elements from each file. The extracted data elements can be placed in a database memory (e.g., database 226) of system 1.

After obtaining and processing the claims data, system 1 can determine a grouping for one or more patients (502). In one non-limiting example, the grouping could correspond to the different groups (and group numbers) shown in the table above and discussed herein. System 1 may use the particular grouping to determine if and when a particular intervention should be carried out for a given patient.

As explained herein, determining a grouping for a particular patient may take a variety of factors into account. As a non-limiting example, system 1 may take into account a timing component and/or a risk component in determining whether to put a patient in a particular group. It should be appreciated that a patient may be considered as falling within three general risk categories that include, but are not limited to, a patient requiring intervention, a patient not requiring an intervention though the intervention may help the patient, and/or the patient having limited value in an intervention. System 1 may assign the patient to a particular grouping that can generally correspond to one of these three risk categories.

As discussed herein, the timing component and the risk component can be used to determine (or explain) why a patient is assigned to a particular group. System 1 can use claims data to determine aspects related to the timing component and/or the risk component. For example, system 1 can use the obtained and processed claims data to identify patients on a particular medication (or several medications). In one non-limiting example, system 1 may use NDC drug code 411 to identify a type of medication and then determine which patients are using (or have been prescribed) the medication.

Using additional information in the claims data, system 1 may determine when the user filled the medication (e.g., service date or fill date 404) as well as the prescription date (e.g., prescription date 406) to understand a filling history of the patient as well as the period in time in which the patient may be due for filling a medication. For example, system 1 may use the current date (or future date(s)) to approximate where a patient may be at in their fill cycle for a medication, based on information from days supply 408 and/or service date or fill date 404.

As a specific example, a patient may be prescribed a 90 day supply of a given medication where the patient will be at different points of a fill cycle within that 90 days. As discussed herein, the patient may be in a "fill eligible window" (e.g., medication is ready to be refilled), a "proactive" window (e.g., before a "fill eligible" window), or an "out of drug" window (e.g., patient is determined as out of a drug based on the claims data). Determining which "window" of a fill cycle the user may correspond can help determine, at least, the timing component associated with a grouping. For example, if the patient's medication is not ready to be refilled, they will be in the "proactive" window and, depending upon patient history, may not be prioritized for an intervention. That is, the patient may have lower priority compared to other patients for recommending an intervention.

Likewise, if the patient's medication is ready to be filled (but not out of the drug), the patient will be in the "fill eligible" window and thus there is an increased likelihood that the patient is prioritized for an intervention. That is, the patient may have a higher priority compared to other patients for recommending an intervention. If the patient is "out of drug" (e.g., patient is determined as out of a drug based on the claims data), the patient may be at an even higher likelihood of being prioritized for receiving an intervention (or several interventions). This example is of course non-limiting and the technology described herein envisions any variety of methods for prioritizing a patient for recommending intervention.

The system 1 may also use the claims data to determine if the patient is a higher risk of being non-adherent to a medication than others (e.g., the risk component). In one non-limiting example, the risk component may relate to a variety of factors associated with a medication and a patient including, but not limited to, the medication type, a patient history of filling a medication, and/or demographic information associated with the patient (e.g., patient age). For example, system 1 can use information from the pharmacy claims data to determine if the patient has been timely at filling a particular medication. As a specific example, a patient may be due to refill a medication by April 1 but may not have actually refilled the medication until April 15. The patient may then be determined as being late on refilling the medication and thus put in a higher risk category than before (e.g., from "low" to "moderate" risk, or from "moderate" to "high" risk). Thus, using such historical information of the patient, system 1 may better determine the risk component associated with the patient. As mentioned above, other supplemental information can be used to provide additional information as to why a patient is associated with a particular grouping. For example, information related to whether a member is filling at multiple pharmacies and/or is new to a health plan can also be used to help explain the grouping for a patient.

Using at least the timing component and the risk component, the system 1 can determine which grouping to place a particular patient. As a non-limiting example, system 1 could place a low risk patient that is in the "proactive" window in a lower prioritized grouping (e.g., group 4). Likewise, system 1 could place a high risk patient that is in the "fill eligible" window in a higher prioritized grouping (e.g., groups 1 or 2). As mentioned herein, the patient may change groupings depending on how factors related to the timing component and the risk component, may change over time. That is, the grouping for the patient is not static and may change dynamically over time.

After determining a grouping for a patient, system 1 may prioritize the patient based on the determined grouping (503). In one non-limiting example, the system 1 can determine the timing and/or frequency of interventions depending upon the grouping of the patient at a given point in time. As a specific example, if the patient is in groups 1 or 2, system 1 may prioritize the patient to recommend at least one intervention in order to have the patient become more adherent to a medication. Likewise, if the patient is in group 4, system 1 may assign a lower priority to the patient for recommending intervention (e.g., not recommend that any intervention be made to the patient, at least until a later point in time).

System 1 can take into account criteria related to a specific intervention provided (e.g., live telephone calls versus text messages) and modify the patient prioritization accordingly (504). For example, system 1 may determine that member abrasion for a patient may be high for a live telephone call and have lower prioritization for this intervention type (e.g., patient recently received a live call). Thus, system 1 may lower priority of the patient to take into account the criteria associated with a specific intervention. Moreover, system 1 may impose a "cap" on a type and/or total number of interventions within a given period of time (e.g., a "do not call barrier"). For example, system 1 may limit the total number of calls recommended for a patient within a three month period in order to prevent any member abrasion (thus resulting in a member ignoring future calls and/or asking to opt out of any further communications).

It should be appreciated that a member may be recommended for intervention multiple times in a short time period only when necessary (e.g., when "out of drug"). Likewise, system 1 may use the patient fill history and/or other factors to "learn" certain patient behavior and can update and modify priority for recommendation using various dynamic learning techniques. For example, system 1 can change a weighting of a patient over time based on patient response to an intervention. That is, system 1 may generate an intervention recommendation and, based on patient response, system 1 may alter a weight/score associated with the patient based on the patient response to intervention. For example, a patient who was previously contacted repeatedly when "out of drug" but did not refill their medication after intervention may have lower priority the next time they are "out of drug." Moreover, as system 1 prioritizes the members based on their associated grouping, each member with a high risk of non-adherence belonging to a particular health care provider should receive some type of intervention within a given year, assuming sufficient capacity for the provider.

System 1 may then generate output data (505) associated with an intervention recommendation. Such aspects of output data are discussed in more detail with respect to the example user interface components, in FIGS. 6A-D, discussed below.

FIGS. 6A-D show non-limiting example user interface(s) 600 generated by system 1. In one non-limiting example, user interface(s) 600 (hereinafter referred to as "user interface" 600) can be generated by system 1 and transmitted as data packets to one or more client devices (e.g., client device 210) where client devices can use the data packets to render the user interface 600. User interface 600 can display different details regarding a patient medical history where such information may be reviewable by an end user (e.g., pharmacists). It should be appreciated that the information shown in user interface 600 may be generated from the claims data obtained and stored by system 1. It should be further appreciated that similar user interfaces are also described and shown in detail in related U.S. patent application Ser. Nos. 14/319,450, 15/928,763, and 17/142,480 (incorporated herein by reference).

Figure 6A:
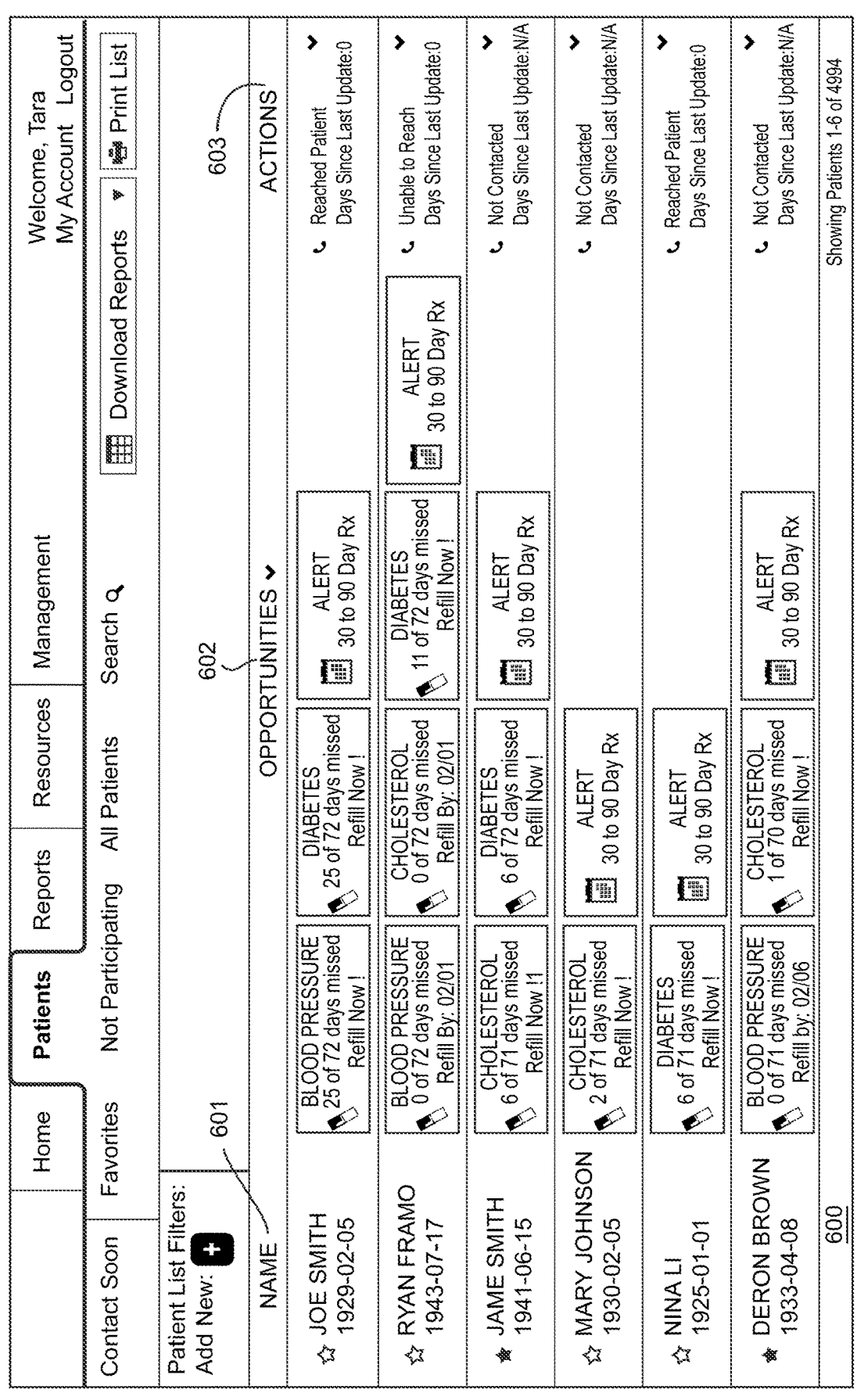
Figure 7:
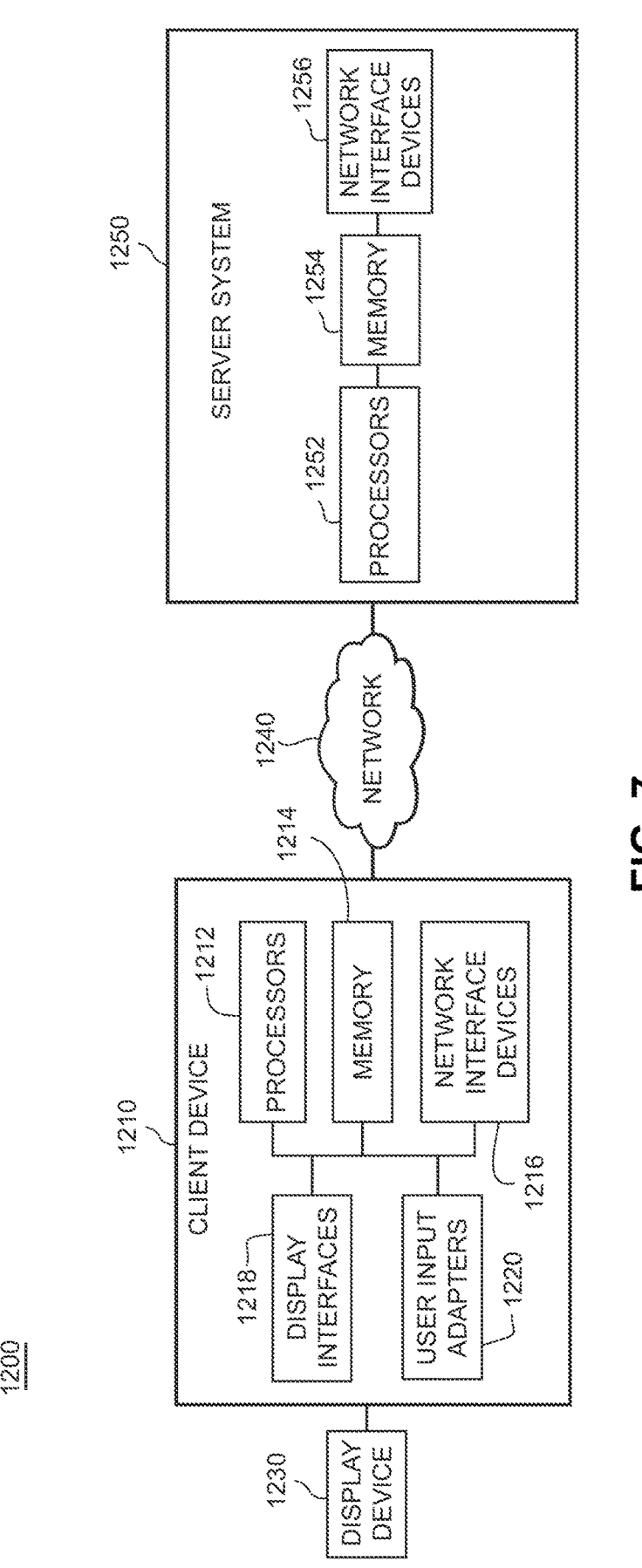
FIG. 7 shows a non-limiting example block diagram of hardware components comprising the system shown in FIG. 2.

FIG. 6A specifically shows one view of the user interface 600 where different medication information for a patient(s) is compiled and summarized. The example shown in FIG. 6A depicts a user interface 600 that includes a listing of patients where each listing depicts associated medication use. As mentioned herein, the listing of patients may be prioritized by system 1 based on the associated grouping for each patient. User interface 600 shows the listing of patients where each patient name 601 is displayed. The patient name 601 can include a full name of the patient and a patient date-of-birth. User interface 600 further includes therapies 602 which could include one or more therapies (e.g., medications) which the patient is using. Each patient may have a single (or multiple) associated therapies depicted in therapies 602 where each element in therapies 602 can display different information associated with a respective therapy. For example, each element in therapies 602 could include an identification of a medication (or medication type) associated with a patient (e.g., blood pressure medication, diabetes medication). Therapies 602 can include an indication of "days missed" related to a number of days past an expected refill date for the medication. Therapies 602 can further include an indication as to whether (or when) the medication should be refilled.

Using the example from FIG. 6A, patient "Joe Smith" is taking a variety of therapies that include blood pressure medication and diabetes medication. Based on user input associated with user interface 600, further views of the user interface 600 may be displayed to a user showing greater detail regarding medication use. User interface 600 may also include actions 603 indicating whether any particular actions have been taken in association with patient outreach. In one example, actions 603 may indicate whether a medical professional has conducted any outreach/intervention with the patient and/or has counseled the patient regarding medication use, among other examples.

Figure 6B:
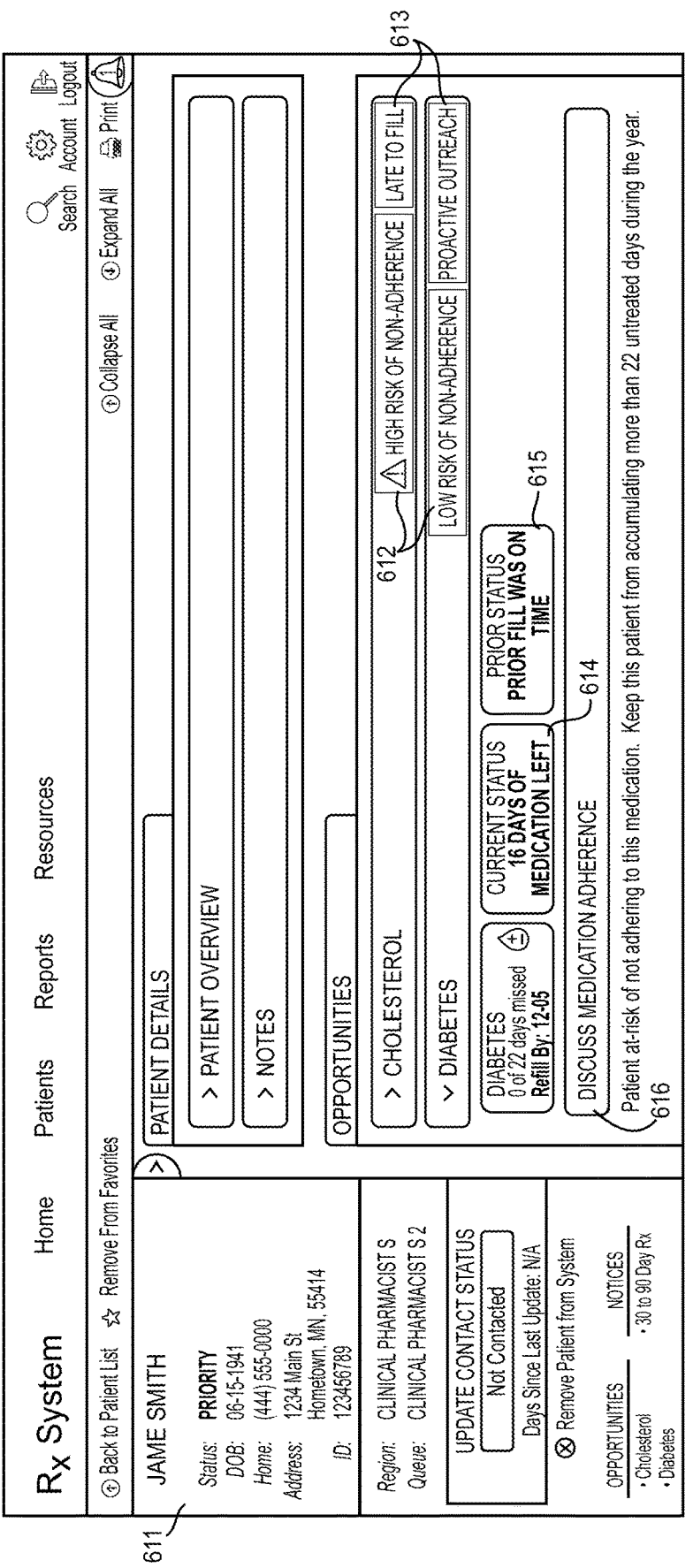

FIG. 6B shows another non-limiting view of the example user interface 600. FIG. 6B specifically shows an example user interface of a patient level detail showing different information associated with a specific patient. The example user interface 600 shown in FIG. 6B may be generated when a specific patient is selected from the listing shown in FIG. 6A. This example is of course non-limiting and the technology described herein envisions any variety of manner in which the user interface 600 in FIG. 6B can be generated including, but not limited to, specific input of a user name and/or user identifier.

User interface 600 in FIG. 6B shows a patient details 611 portion including certain detailed information of a patient that can include a patient name, date of birth, patient status (e.g., priority, non-priority), phone number, and/or address information. The user interface 600 can include a selection box in or near patient details 611 allowing for updating as to whether the patient has been contacted (e.g., under "update contact status").

User interface 600 in FIG. 6B also shows different opportunity elements (e.g., within the "opportunities" area) that include visual details related to the user status for one or more medications. User interface 600 can include adherence risk 612 elements that can show a risk level related to adherence for a patient for a particular medication (e.g., low risk, moderate risk, high risk, no risk). User interface 600 can also include an outreach type 613 element that can indicate the type of outreach for the patient for a particular medication. For example, outreach type 613 can include a display for "late fill," "ready for fill," and/or "proactive outreach" depending upon the patient(s) prescription status. In one non-limiting example, the different adherence risk 612 and outreach type 613 can describe the patient outreach level as well as a solution for performing the outreach. For example, a patient that is late to fill indicates the patient is out of a medication and the user can be instructed to discuss with the patient if they are taking the medication as prescribed and about how the patient plans to refill the medication. A patient that is ready to fill is indicative of a patient having a few units of a medication available (e.g., a few pills "on hand") but is eligible for a new fill in accordance with their insurance benefits. If the patient was also a high risk of non-adherence, the user can be instructed to encourage the patient to fill the next fill on time and help them to resolve any barriers that would lead them to being late to fill the prescription. A patient that is a high risk of non-adherence and in proactive outreach may be indicative of the patient currently still having available medication but, based on predictive analytics, is at risk for non-adherence in the future. In this case, the user may be instructed to identify ways to encourage the patient to be adherent, with the conversation focusing less on a next fill and more on a holistic approach to medication usage.

User interface 600 in FIG. 6B may also show current status 614 and prior status 615 related to prescription fill information. In the example shown in FIG. 6B, current status 614 indicates the current fill status for diabetes medication and indicates there are 16 days left for the medication. Prior status 615 can show information related to a previous fill cycle and the example of FIG. 6B shows prior status 615 as being "on time" for the patient of interest. Such information can facilitate current outreach and inform a user as to whether any certain pattern(s) of behavior exists for a patient. These therapy level detail examples can include a patient being "out of medication" or having "X" days of medication left (e.g., in the current status 614 portion), and a prior fill being "X" days late, prior fill was "on time," or "N/A" if no prior fill (e.g., in the prior status 615 portion). Certain additional reasons could be displayed that could include, but are not limited to, patient being non-adherent in a previous year, multiple doses having been recently dispensed, and/or patient being new to a therapy.

User interface 600 can also show a discussion portion 616 showing advice regarding whether medication adherence should be discussed with the patient. In the example of FIG. 6B, the patient is shown as being "at-risk" of not adhering to the diabetes medication and the user is advised to prevent the patient from accumulating more than 22 untreated days during the year. The discussion portion 616 can include any variety of information related to the patient in which a user should discuss with the patient (e.g., particularly associated with a discussion of medication adherence).

Figure 6C:
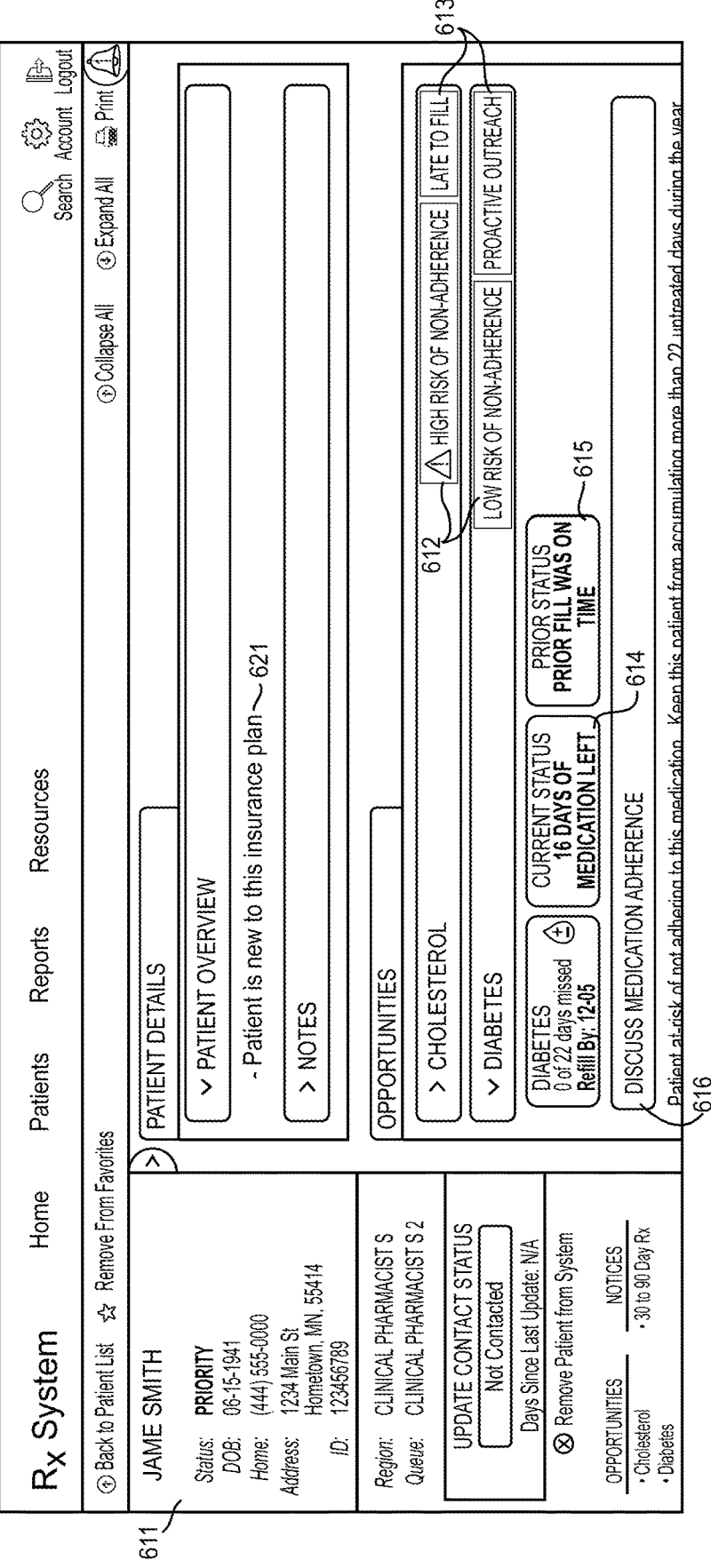

FIG. 6C shows a non-limiting example user interface 600 where a portion of the user interface 600 is shown. In the example of FIG. 6C, user interface 600 includes a patient overview 621 portion that includes certain information associated with the patient. In the example of FIG. 6C, patient overview 621 indicates that the patient is new to an insurance plan and can display other various information for the patient. For example, certain patient highlights such as the patient being new to a health plan and/or multiple pharmacies can be shown in the patient overview 621 portion in a patient profile. It should be appreciated that patient overview portion 621 can be integrated in the user interface 600 shown in FIG. 6B, but providing various information when the "patient overview" element is selected. For example, user input associated with the "patient overview" area in user interface 600 may cause the displayed elements to "drop down" additional information associated with patient overview portion 621.

FIG. 6D shows another non-limiting example user interface 600 showing various additional patient information. The example user interface 600 shown in FIG. 6D may show various "essential" information for the patient and can include certain elements related to patient intervention (or outreach). User interface 600 can include another adherence risk 631 and outreach type 632 showing different risks of adherence and specific outreach windows, respectively, for a patient. Similar to FIG. 6B, adherence risk 631 elements can show a risk level related to adherence for a patient for a particular medication (e.g., low risk, moderate risk, high risk, no risk). Outreach type 632 elements can indicate the type of outreach for the patient for a particular medication. For example, outreach type 632 can include a display for "late fill," "ready for fill," and/or "proactive outreach" depending upon the patient(s) prescription status.

It should be appreciated that the information presented in FIG. 6D can be integrated in the user interface 600 shown in FIG. 6B. For example, the information presented in FIG. 6D can be positioned below the interface elements shown in FIG. 6B and, as the user "scrolls" down, the elements shown in FIG. 6D may be emphasized. For example, FIG. 6D shows a "medication adherence" portion with different associated therapies. The portion shown in FIG. 6D may be within the interface 600 shown in FIG. 6B, but displayed as the user scrolls down in the interface. This example is of course non-limiting, and the technology described herein envisions and variety of mechanisms for displaying the information shown in FIG. 6D.

As can be seen in FIG. 6D, user interface 600 displays information associated with medication adherence, where different therapies are identified. Within each therapy is an adherence risk 631 element and outreach type 632 element. Each therapy can also include overview information including, but not limited to, medication status, index date, next fill due date, and/or conversion eligibility information. Likewise, each therapy can include various fill detail information associated with the therapy. For example, fill detail information can include a fill date, an identification of a specific medication associated with the therapy, a days supply, a quantity dispensed, a prescriber identification, a pharmacy identification, and/or a next due date (e.g., for when the medication should be refilled). The examples shown in FIGS. 6A-D are of course non-limiting and the technology described herein envisions any type of user interface 600 that can be displayed and show patient related information.

FIG. 7 shows a non-limiting example block diagram of a hardware architecture for the system 1200. In the example shown in FIG. 7, the client device 1210 communicates with a server system 1250 via a network 1240. The network 1240 could comprise a network of interconnected computing devices, such as the internet. The network 1240 could also comprise a local area network (LAN) or could comprise a peer-to-peer connection between the client device 1210 and the server system 1250. As will be described below, the hardware elements shown in FIG. 8 could be used to implement the various software components and actions shown and described above as being included in and/or executed at the client device 1210 and server system 1250.

In some embodiments, the client device 1210 (which may also be referred to as "client system" herein) includes one or more of the following: one or more processors 1212; one or more memory devices 1214; one or more network interface devices 1216; one or more display interfaces 1218; and one or more user input adapters 1220. Additionally, in some embodiments, the client device 1210 is connected to or includes a display device 1230. As will explained below, these elements (e.g., the processors 1212, memory devices 1214, network interface devices 1216, display interfaces 1218, user input adapters 1220, display device 1230) are hardware devices (for example, electronic circuits or combinations of circuits) that are configured to perform various different functions for the computing device 1210.

In some embodiments, each or any of the processors 1212 is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, or a system-on-a-chip (SOC) (e.g., an integrated circuit that includes a CPU and other hardware components such as memory, networking interfaces, and the like). And/or, in some embodiments, each or any of the processors 1212 uses an instruction set architecture such as x86 or Advanced RISC Machine (ARM).

In some embodiments, each or any of the memory devices 1214 is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions), or other type of device that performs the volatile or non-volatile storage of data and/or instructions (e.g., software that is executed on or by processors 1212). Memory devices 1214 are examples of non-volatile computer-readable storage media.

In some embodiments, each or any of the network interface devices 1216 includes one or more circuits (such as a baseband processor and/or a wired or wireless transceiver), and implements layer one, layer two, and/or higher layers for one or more wired communications technologies (such as Ethernet (IEEE 802.3)) and/or wireless communications technologies (such as Bluetooth, WiFi (IEEE 802.11), GSM, CDMA2000, UMTS, LTE, LTE-Advanced (LTE-A), and/or other short-range, mid-range, and/or long-range wireless communications technologies). Transceivers may comprise circuitry for a transmitter and a receiver. The transmitter and receiver may share a common housing and may share some or all of the circuitry in the housing to perform transmission and reception. In some embodiments, the transmitter and receiver of a transceiver may not share any common circuitry and/or may be in the same or separate housings.

In some embodiments, each or any of the display interfaces 1218 is or includes one or more circuits that receive data from the processors 1212, generate (e.g., via a discrete GPU, an integrated GPU, a CPU executing graphical processing, or the like) corresponding image data based on the received data, and/or output (e.g., a High-Definition Multimedia Interface (HDMI), a DisplayPort Interface, a Video Graphics Array (VGA) interface, a Digital Video Interface (DVI), or the like), the generated image data to the display device 1230, which displays the image data. Alternatively or additionally, in some embodiments, each or any of the display interfaces 1218 is or includes, for example, a video card, video adapter, or graphics processing unit (GPU).

In some embodiments, each or any of the user input adapters 1220 is or includes one or more circuits that receive and process user input data from one or more user input devices (not shown in FIG. 8) that are included in, attached to, or otherwise in communication with the client device 1210, and that output data based on the received input data to the processors 1212. Alternatively or additionally, in some embodiments each or any of the user input adapters 1220 is or includes, for example, a PS/2 interface, a USB interface, a touchscreen controller, or the like; and/or the user input adapters 1220 facilitates input from user input devices (not shown in FIG. 7) such as, for example, a keyboard, mouse, trackpad, touchscreen, etc. . . . .

In some embodiments, the display device 1230 may be a Liquid Crystal Display (LCD) display, Light Emitting Diode (LED) display, or other type of display device. In embodiments where the display device 1230 is a component of the client device 1210 (e.g., the computing device and the display device are included in a unified housing), the display device 1230 may be a touchscreen display or non-touchscreen display. In embodiments where the display device 1230 is connected to the client device 1210 (e.g., is external to the client device 1210 and communicates with the client device 1210 via a wire and/or via wireless communication technology), the display device 1230 is, for example, an external monitor, projector, television, display screen, etc. . . . .

In various embodiments, the client device 1210 includes one, or two, or three, four, or more of each or any of the above-mentioned elements (e.g., the processors 1212, memory devices 1214, network interface devices 1216, display interfaces 1218, and user input adapters 1220). Alternatively or additionally, in some embodiments, the client device 1210 includes one or more of: a processing system that includes the processors 1212; a memory or storage system that includes the memory devices 1214; and a network interface system that includes the network interface devices 1216.

The client device 1210 may be arranged, in various embodiments, in many different ways. As just one example, the client device 1210 may be arranged such that the processors 1212 include: a multi (or single)-core processor; a first network interface device (which implements, for example, WiFi, Bluetooth, NFC, etc. . . . ); a second network interface device that implements one or more cellular communication technologies (e.g., 3G, 4G LTE, CDMA, etc. . . . ); memory or storage devices (e.g., RAM, flash memory, or a hard disk). The processor, the first network interface device, the second network interface device, and the memory devices may be integrated as part of the same SOC (e.g., one integrated circuit chip). As another example, the client device 1210 may be arranged such that: the processors 1212 include two, three, four, five, or more multi-core processors; the network interface devices 1216 include a first network interface device that implements Ethernet and a second network interface device that implements WiFi and/or Bluetooth; and the memory devices 1214 include a RAM and a flash memory or hard disk.

Server system 1250 also comprises various hardware components used to implement the software elements for server system 200 of FIG. 2. In some embodiments, the server system 1250 (which may also be referred to as "server device" herein) includes one or more of the following: one or more processors 1252; one or more memory devices 1254; and one or more network interface devices 1256. As will explained below, these elements (e.g., the processors 1252, memory devices 1254, network interface devices 1256) are hardware devices (for example, electronic circuits or combinations of circuits) that are configured to perform various different functions for the server system 1250.

In some embodiments, each or any of the processors 1252 is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, or a system-on-a-chip (SOC) (e.g., an integrated circuit that includes a CPU and other hardware components such as memory, networking interfaces, and the like). And/or, in some embodiments, each or any of the processors 1252 uses an instruction set architecture such as x86 or Advanced RISC Machine (ARM).

In some embodiments, each or any of the memory devices 1254 is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions), or other type of device that performs the volatile or non-volatile storage of data and/or instructions (e.g., software that is executed on or by processors 1252). Memory devices 1254 are examples of non-volatile computer-readable storage media.

In some embodiments, each or any of the network interface devices 1256 includes one or more circuits (such as a baseband processor and/or a wired or wireless transceiver), and implements layer one, layer two, and/or higher layers for one or more wired communications technologies (such as Ethernet (IEEE 802.3)) and/or wireless communications technologies (such as Bluetooth, WiFi (IEEE 802.11), GSM, CDMA2000, UMTS, LTE, LTE-Advanced (LTE-A), and/or other short-range, mid-range, and/or long-range wireless communications technologies). Transceivers may comprise circuitry for a transmitter and a receiver. The transmitter and receiver may share a common housing and may share some or all of the circuitry in the housing to perform transmission and reception. In some embodiments, the transmitter and receiver of a transceiver may not share any common circuitry and/or may be in the same or separate housings.

In various embodiments, the server system 1250 includes one, or two, or three, four, or more of each or any of the above-mentioned elements (e.g., the processors 1252, memory devices 1254, network interface devices 1256). Alternatively or additionally, in some embodiments, the server system 1250 includes one or more of: a processing system that includes the processors 1252; a memory or storage system that includes the memory devices 1254; and a network interface system that includes the network interface devices 1256.

The server system 1250 may be arranged, in various embodiments, in many different ways. As just one example, the server system 1250 may be arranged such that the processors 1252 include: a multi (or single)-core processor; a first network interface device (which implements, for example, WiFi, Bluetooth, NFC, etc. . . . ); a second network interface device that implements one or more cellular communication technologies (e.g., 3G, 4G LTE, CDMA, etc. . . . ); memory or storage devices (e.g., RAM, flash memory, or a hard disk). The processor, the first network interface device, the second network interface device, and the memory devices may be integrated as part of the same SOC (e.g., one integrated circuit chip). As another example, the server system 1250 may be arranged such that: the processors 1252 include two, three, four, five, or more multi-core processors; the network interface devices 1256 include a first network interface device that implements Ethernet and a second network interface device that implements WiFi and/or Bluetooth; and the memory devices 1254 include a RAM and a flash memory or hard disk.

As previously noted, whenever it is described in this document that a software module or software process performs any action, the action is in actuality performed by underlying hardware elements according to the instructions that comprise the software module. Consistent with the foregoing, in various embodiments, each or any combination of the client device 210 or the server system 220, each of which will be referred to individually for clarity as a "component" for the remainder of this paragraph, are implemented using an example of the client device 1210 or the server system 1250 of FIG. 7. In such embodiments, the following applies for each component: (a) the elements of the client device 1210 shown in FIG. 7 (i.e., the one or more processors 1212, one or more memory devices 1214, one or more network interface devices 1216, one or more display interfaces 1218, and one or more user input adapters 1220) and the elements of the server system 1250 (i.e., the one or more processors 1252, one or more memory devices 1254, one or more network interface devices 1256), or appropriate combinations or subsets of the foregoing, are configured to, adapted to, and/or programmed to implement each or any combination of the actions, activities, or features described herein as performed by the component and/or by any software modules described herein as included within the component; (b) alternatively or additionally, to the extent it is described herein that one or more software modules exist within the component, in some embodiments, such software modules (as well as any data described herein as handled and/or used by the software modules) are stored in the respective memory devices (e.g., in various embodiments, in a volatile memory device such as a RAM or an instruction register and/or in a non-volatile memory device such as a flash memory or hard disk) and all actions described herein as performed by the software modules are performed by the respective processors in conjunction with, as appropriate, the other elements in and/or connected to the client device 1210 or server system 1250; (c) alternatively or additionally, to the extent it is described herein that the component processes and/or otherwise handles data, in some embodiments, such data is stored in the respective memory devices (e.g., in some embodiments, in a volatile memory device such as a RAM and/or in a non-volatile memory device such as a flash memory or hard disk) and/or is processed/handled by the respective processors in conjunction, as appropriate, the other elements in and/or connected to the client device 1210 or server system 1250; (d) alternatively or additionally, in some embodiments, the respective memory devices store instructions that, when executed by the respective processors, cause the processors to perform, in conjunction with, as appropriate, the other elements in and/or connected to the client device 1210 or server system 1250, each or any combination of actions described herein as performed by the component and/or by any software modules described herein as included within the component.

The hardware configurations shown in FIG. 7 and described above are provided as examples, and the subject matter described herein may be utilized in conjunction with a variety of different hardware architectures and elements. For example: in many of the Figures in this document, individual functional/action blocks are shown; in various embodiments, the functions of those blocks may be implemented using (a) individual hardware circuits, (b) using an application specific integrated circuit (ASIC) specifically configured to perform the described functions/actions, (c) using one or more digital signal processors (DSPs) specifically configured to perform the described functions/actions, (d) using the hardware configuration described above with reference to FIG. 7, (e) via other hardware arrangements, architectures, and configurations, and/or via combinations of the technology described in (a) through (e).

Technical Advantages of Described Subject Matter

The technology described herein allows for efficient storage and processing of claims data and improves the system's ability to display information and interact with a user. In particular, the system can process large volumes of claims data elements and efficiently store the same in a database managed by the system so that the data can be used to generate a user interface. In doing so, the system efficiently stores, organizes, and manages large volumes of data by breaking the data down into understandable components that are used in fast and efficient generation of a display presenting the data. More specifically, the system enables more efficient storage of data in the memory of the system thus providing an enhanced computer memory system.

It should be appreciated that the technology advantageously improves the timing in which a user will be recommended to conduct an outreach with a member. In doing so, user interaction with the system (e.g., accessing patient history) will be reduced and thus the overall communication between a user device (e.g., client device) and the system (e.g., server system) will be more efficient. Thus, the communication latency within the system is improved thereby improving the overall communication capability of the system.

The technology described herein also provides an easy-to-use user interface that includes a new and useful presentation of information, as well as a new and useful method for processing data compared to the conventional technology. Additionally, the improved user interface includes various graphical and interactive elements associated with medication adherence as well as intervention recommendations associated with the groupings described herein, among other aspects. The user interface thus improves the overall human-computer interaction and provides an easy-to-use mechanism for an end user to understand highly complicated information.

Selected Definitions

Whenever it is described in this document that a given item is present in "some embodiments," "various embodiments," "certain embodiments," "certain example embodiments," "some example embodiments," "an exemplary embodiment," or whenever any other similar language is used, it should be understood that the given item is present in at least one embodiment, though is not necessarily present in all embodiments. Consistent with the foregoing, whenever it is described in this document that an action "may," "can," or "could" be performed, that a feature, element, or component "may," "can," or "could" be included in or is applicable to a given context, that a given item "may," "can," or "could" possess a given attribute, or whenever any similar phrase involving the term "may," "can," or "could" is used, it should be understood that the given action, feature, element, component, attribute, etc. is present in at least one embodiment, though is not necessarily present in all embodiments. Terms and phrases used in this document, and variations thereof, unless otherwise expressly stated, should be construed as open-ended rather than limiting. As examples of the foregoing: "and/or" includes any and all combinations of one or more of the associated listed items (e.g., a and/or b means a, b, or a and b); the singular forms "a", "an" and "the" should be read as meaning "at least one," "one or more," or the like; the term "example" is used provide examples of the subject under discussion, not an exhaustive or limiting list thereof; the terms "comprise" and "include" (and other conjugations and other variations thereof) specify the presence of the associated listed items but do not preclude the presence or addition of one or more other items; and if an item is described as "optional," such description should not be understood to indicate that other items are also not optional.

As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

Further Applications of Described Subject Matter

Although a number of references are made in this document to web applications, it should be understood that the features described herein may also be used, in various embodiments, in the context of other types of applications such as applications that are deployed/installed as binaries on client systems.

Although process steps, algorithms or the like, including without limitation with reference to FIGS. 1-7, may be described or claimed in a particular sequential order, such processes may be configured to work in different orders. In other words, any sequence or order of steps that may be explicitly described or claimed in this document does not necessarily indicate a requirement that the steps be performed in that order; rather, the steps of processes described herein may be performed in any order possible. Further, some steps may be performed simultaneously (or in parallel) despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary, and does not imply that the illustrated process is preferred.

Although various embodiments have been shown and described in detail, the claims are not limited to any particular embodiment or example. None of the above description should be read as implying that any particular element, step, range, or function is essential. All structural and functional equivalents to the elements of the above-described embodiments that are known to those of ordinary skill in the art are expressly incorporated herein by reference and are intended to be encompassed Moreover, it is not necessary for a device or method to address each and every problem sought to be solved by the present invention, for it to be encompassed by the invention. No embodiment, feature, element, component, or step in this document is intended to be dedicated to the public.

While the technology has been described in connection with what is presently considered to be an illustrative practical and preferred embodiment, it is to be understood that the technology is not to be limited to the disclosed embodiment, but on the contrary, is intended to cover various modifications and equivalent arrangements.

The invention claimed is:

1. A system, comprising:

a processor; and a memory configured to store computer readable instructions that, when executed by the processor, cause the system to:

obtain claims data, associated with a first patient from a plurality of patients, from one or more data sources;

parse the claims data and extract claims data elements associated with the one or more patients and store the claims data elements in a database of the system;

identify a first medication associated with the first patient using a national drug code (NDC) identifier from the claims data elements;

identify a fill window for the first medication using, at least, a fill date and a days supply from the claims data elements;

identify, a timing component, for timings associated with recommending an intervention associated with the first medication for the first patient, using, at least, the identified fill window for the first medication;

identify, using, at least, a member date of birth and the fill date from the claims data elements, a risk component based on an amount of risk of medication adherence associated with the first medication for the first patient;

identify, using the claims data elements, supplemental information associated with the first patient;

assign a group number, from a set of group numbers, to the first patient based on, at least, the timing component, the risk component, and the supplemental information, wherein the set of group numbers are used to prioritize a listing of patients for recommending intervention;

using at least the group number, determine whether to recommend the intervention associated with the first medication for the first patient; and generate user interface data associated with a user interface, wherein the user interface includes a plurality of views, and at least a first view of the user interface includes:

a first portion having a listing of patients including the first patient, wherein each listing includes an identification of a patient, at least one medication associated with the patient, and an indication related to medication adherence associated with the patient, wherein upon selection of the first patient, the user interface is configured to switch from the first view to a second view, wherein the second view of the user interface includes:

a first portion having the one or more medications associated with the first patient, wherein each medication, from the one or more medications, includes an indication associated with the risk of non-adherence to the medication and an indication of outreach type associated with the intervention, and selection of a medication, from the one or more medications, causes generation of additional display showing a first object having an identification of the medication and a refill date associated with the medication, a second object having a current status indication including at least a days supply associated with the medication, and a third object having a prior status indication associated with fill status for the medication, wherein the additional display further includes a discussion portion indicating whether medication adherence should be discussed with the first patient, and the user interface is configured to update the second view to display, for each medication, medication detail information, wherein the medication detail information for each medication includes at least:

a first portion having medication overview information that includes, at least, an index date and a next fill date for the medication, and a second portion having fill detail information that includes, at least, a line item listing of fill details for each medication wherein each item, in the line item listing, includes at least a fill date, identification of the medication and dosage amount, a days supply for the medication, a quantity dispensed for the medication, an identification of a prescriber of the medication, an identification of a pharmacy associated with the medication, and a next due date for the medication.

2. The system of claim 1, wherein the system is configured to change group numbers to the patient over time.

3. The system of claim 1, wherein the group number is associated with an importance level for carrying out the intervention for the patient.

4. The system of claim 1, wherein the system utilizes a learning model to adapt to specific behavior for the patient.

5. The system of claim 1, wherein assignment of the group number to each patient includes taking into account patient abrasion from intervention associated with each patient.

6. The system of claim 1, wherein determining whether to recommend the intervention includes determining priority of the intervention for each patient based on the group number and/or the stored information.

7. The system of claim 1, wherein the timing component includes, at least, a therapy recommendation being early, a therapy intervention is recommended to discuss with a patient because the patient is able to pick up one or more medications at a certain time, and/or a therapy is recommended to discuss with the patient because the patient is currently late to pick up one or more medications.

8. The system of claim 1, wherein the risk component is based on a medication fill history, associated with each patient, over a specified period of time.

9. The system of claim 1, wherein the risk component includes, at least, a therapy being low risk of non-adherence for a specified period of time, the therapy being moderate risk of non-adherence for the specified period of time, and/or the therapy being high risk of non-adherence for the specified period of time.

10. The system of claim 1, wherein the supplemental information includes, at least, information associated with a patient filling at multiple pharmacies and/or a patient being new to a health plan.

11. The system of claim 1, wherein the next fill date, in the medication overview information, further includes an indication in number of days until the next fill date or an indication in number of days late from the next fill date.

12. The system of claim 1, wherein the fill window includes, at least, a proactive window, a fill eligible window, and an out of drug window.

13. A method for generating output data associated with targeted intervention, the method comprising:

at an information processing system having a processor and a memory:

obtaining claims data, associated with a first patient from a plurality of patients, from one or more data sources;

parsing the claims data and extract claims data elements associated with the one or more patients and store the claims data elements in a database of the system;

identifying a first medication associated with the first patient using a national drug code (NDC) identifier from the claims data elements;

identifying a fill window for the first medication using, at least, a fill date and a days supply from the claims data elements;

identifying a timing component, for timings associated with recommending an intervention associated with the first medication for the first patient, using, at least, the identified fill window for the first medication;

identifying, using, at least, a member date of birth and the fill date from the claims data elements, a risk component based on an amount of risk of medication adherence associated with the first medication for the first patient;

assigning a group number, from a set of group numbers, to the first patient based on, at least, the timing component and the risk component, wherein the set of group numbers are used to prioritize a listing of patients for recommending intervention;

using at least the group number, determining whether to recommend the intervention associated with the first medication for the first patient; and generating user interface data associated with a user interface, wherein the user interface includes a plurality of views, and at least a first view of the user interface includes:

a first portion having a listing of patients including the first patient, wherein each listing includes an identification of a patient, at least one medication associated with the patient, and an indication related to medication adherence associated with the patient, wherein upon selection of the first patient, the user interface is configured to switch from the first view to a second view, wherein the second view of the user interface includes:

a first portion having the one or more medications associated with the first patient, wherein each medication, from the one or more medications, includes an indication associated with the risk of non-adherence to the medication and an indication of outreach type associated with the intervention, and selection of a medication, from the one or more medications, causes generation of additional display showing a first object having an identification of the medication and a refill date associated with the medication, a second object having a current status indication including at least a days supply associated with the medication, and a third object having a prior status indication associated with fill status for the medication, and the user interface is configured to update the second view to display, for each medication, medication detail information, wherein the medication detail information for each medication includes at least:

a first portion having medication overview information that includes, at least, an index date and a next fill date for the medication, and a second portion having fill detail information that includes, at least, a line item listing of fill details for each medication wherein each item, in the line item listing, includes at least a fill date, identification of the medication and dosage amount, a days supply for the medication, a quantity dispensed for the medication, an identification of a prescriber of the medication, an identification of a pharmacy associated with the medication, and a next due date for the medication.

14. The method of claim 13, wherein the group number is associated with an importance level for carrying out the intervention for the patient.

15. The method of claim 13, wherein assignment of the group number to each patient includes taking into account patient abrasion from intervention associated with each patient.

16. The method of claim 13, wherein assignment of the group number to each patient further includes supplemental information associated with each patient.

17. A non-transitory computer readable storage medium storing computer readable instructions that, when executed by a processor of an information processing system, cause the information processing system to provide execution comprising:

obtaining claims data, associated with a first patient from a plurality of patients, from one or more data sources;

parsing the claims data and extract claims data elements associated with the one or more patients and store the claims data elements in a database of the system;

identifying a first medication associated with the first patient using a national drug code (NDC) identifier from the claims data elements;

identifying a fill window for the first medication using, at least, a fill date and a days supply from the claims data elements;

identifying, a timing component, for timings associated with recommending an intervention associated with the first medication for the first patient, using, at least, the identified fill window medication;

identifying, using, at least, a member date of birth and the fill date from the claims data elements, a risk component based on an amount of risk of medication adherence associated with the first medication for the first patient;

assigning a group number, from a set of group numbers, to each patient from the one or more patients based on, at least, the timing component and the risk component, wherein the set of group numbers are used to prioritize a listing of patients for recommend intervention;

using at least the group number, determining whether to recommend the intervention associated with the first medication for the first patient; and generating user interface data associated with a user interface, wherein the user interface includes a plurality of views, and at least a first view of the user interface includes:

a first portion having a listing of patients including the first patient, wherein each listing includes an identification of a patient, at least one medication associated with the patient, and an indication related to medication adherence associated with the patient, wherein

31 upon selection of the first patient, the user interface is configured to switch from the first view to a second view, wherein the second view of the user interface includes:

a first portion having the one or more medications associated with the first patient, wherein each medication, from the one or more medications, includes an indication associated with the risk of non-adherence to the medication and an indication of outreach type associated with the intervention, and selection of a medication, from the one or more medications, causes generation of additional display showing a first object having an identification of the medication and a refill date associated with the medication, a second object having a current status indication including at least a days supply associated with the medication, and a third object having a prior status indication associated with fill status for the medication, and the user interface is configured to update the second view to display, for each medication, medication detail information, wherein the medication detail information for each medication includes at least:

a first portion having medication overview information that includes, at least, an index date and a next fill date for the medication, and a second portion having fill detail information that includes, at least, a line item listing of fill details for each medication wherein each item, in the line item listing, includes at least a fill date, identification of the medication and dosage amount, a days supply for the medication, a quantity dispensed for the medication, an identification of a prescriber of the medication, an identification of a pharmacy associated with the medication, and a next due date for the medication.

18. The non-transitory computer readable storage medium of claim 17, wherein the group number is associated with an importance level for carrying out the intervention for the patient.

19. The non-transitory computer readable storage medium of claim 17, wherein assignment of the group number to each patient includes taking into account patient abrasion from intervention associated with each patient.

20. The non-transitory computer readable storage medium of claim 17, wherein assignment of the group number to each patient further includes supplemental information associated with each patient.

\* \* \* \* \*